US011213675B2

(12) United States Patent
Lee et al.

(10) Patent No.: US 11,213,675 B2
(45) Date of Patent: Jan. 4, 2022

(54) IMPLANTABLE LEAD AFFIXATION STRUCTURE FOR NERVE STIMULATION TO ALLEVIATE BLADDER DYSFUNCTION AND OTHER INDICATION

(71) Applicant: Axonics, Inc., Irvine, CA (US)

(72) Inventors: Henry Lee, Arcadia, CA (US); Alexander Hwu, Anaheim, CA (US)

(73) Assignee: AXONICS, INC., Irvine, CA (US)

(*) Notice: Subject to any disclaimer, the term of this patent is extended or adjusted under 35 U.S.C. 154(b) by 106 days.

(21) Appl. No.: 16/597,470

(22) Filed: Oct. 9, 2019

(65) Prior Publication Data

US 2020/0038652 A1 Feb. 6, 2020

Related U.S. Application Data

(62) Division of application No. 15/719,487, filed on Sep. 28, 2017, now Pat. No. 10,478,619, which is a (Continued)

(51) Int. Cl.
*A61N 1/36* (2006.01)
*A61N 1/05* (2006.01)
(Continued)

(52) U.S. Cl.
CPC ....... *A61N 1/0558* (2013.01); *A61N 1/36007* (2013.01); *A61N 1/36062* (2017.08);
(Continued)

(58) Field of Classification Search
CPC .............. A61N 1/0558; A61N 1/36062; A61N 1/36007; B29C 45/14065;
(Continued)

(56) References Cited

U.S. PATENT DOCUMENTS 3,057,356 A 10/1962 Greatbatch
3,348,548 A 10/1967 Chardack
(Continued)

FOREIGN PATENT DOCUMENTS

AT 520440 9/2011
AU 4664800 11/2000
(Continued)

OTHER PUBLICATIONS

US 9,601,939 B2, 03/2017, Cong et al. (withdrawn)
(Continued)

*Primary Examiner* — Amanda K Hulbert
*Assistant Examiner* — Natasha Patel
(74) *Attorney, Agent, or Firm* — Kilpatrick Townsend & Stockton LLP

(57) ABSTRACT

Anchoring devices for affixing an implanted lead at a target location in a patient are provided herein. Such anchoring devices include a helical body having a plurality of tines extending laterally outward from the lead when deployed that engage tissue to inhibit axial movement of the implanted lead. The plurality of tines are biased towards the laterally extended deployed configuration and fold inward towards the lead to a delivery configuration to facilitate delivery of the lead through a sheath. The tines may be angled in a proximal direction or in both proximal and distal directions and may include various features to assist in visualization and delivery of the lead.

18 Claims, 21 Drawing Sheets

Related U.S. Application Data division of application No. 14/827,074, filed on Aug. 14, 2015, now Pat. No. 9,802,038.

(60) Provisional application No. 62/110,274, filed on Jan. 30, 2015, provisional application No. 62/038,122, filed on Aug. 15, 2014.

(51) Int. Cl.

| | |
|---|---|
| ***B23K 26/38*** | (2014.01) |
| ***B23K 26/40*** | (2014.01) |
| ***B23K 26/242*** | (2014.01) |
| ***B29C 45/14*** | (2006.01) |
| *B29L 31/00* | (2006.01) |
| *B23K 103/14* | (2006.01) |
| *B23K 103/18* | (2006.01) |

(52) U.S. Cl.

CPC ............ *B23K 26/242* (2015.10); *B23K 26/38* (2013.01); *B23K 26/40* (2013.01); *B29C 45/14065* (2013.01); *B29C 45/14598* (2013.01); *B23K 2103/14* (2018.08); *B23K 2103/18* (2018.08); *B23K 2103/26* (2018.08); *B29C 45/14778* (2013.01); *B29L 2031/753* (2013.01)

(58) Field of Classification Search

CPC ........ B29C 45/14598; B29C 45/14778; B23K 26/242; B23K 26/38; B23K 26/40; B23K 2103/14; B23K 2103/18; B23K 2103/26; B29L 2031/753

See application file for complete search history.

(56) References Cited

U.S. PATENT DOCUMENTS 3,646,940 A 3/1972 Timm et al.
3,824,129 A 7/1974 Fagan, Jr.
3,825,015 A 7/1974 Berkovits
3,888,260 A 6/1975 Fischell
3,902,501 A 9/1975 Citron et al.
3,939,843 A 2/1976 Smyth
3,942,535 A 3/1976 Schulman
3,970,912 A 7/1976 Hoffman
3,995,623 A 12/1976 Blake et al.
4,019,518 A 4/1977 Maurer et al.
4,044,774 A 8/1977 Corbin et al.
4,082,097 A 4/1978 Mann et al.
4,141,365 A 2/1979 Fischell et al.
4,166,469 A 9/1979 Littleford
4,269,198 A 5/1981 Stokes
4,285,347 A 8/1981 Hess
4,340,062 A 7/1982 Thompson et al.
4,379,462 A 4/1983 Borkan et al.
4,407,303 A 10/1983 Akerstrom
4,437,475 A 3/1984 White
4,512,351 A 4/1985 Pohndorf
4,550,731 A 11/1985 Batina et al.
4,558,702 A 12/1985 Barreras et al.
4,654,880 A 3/1987 Sontag
4,662,382 A 5/1987 Sluetz et al.
4,719,919 A 1/1988 Marchosky et al.
4,721,118 A 1/1988 Harris
4,722,353 A 2/1988 Sluetz
4,744,371 A 5/1988 Harris
4,800,898 A 1/1989 Hess et al.
4,848,352 A 7/1989 Pohndorf et al.
4,860,446 A 8/1989 Lessar et al.
4,957,118 A 9/1990 Erlebacher
4,989,617 A 2/1991 Memberg et al.
5,012,176 A 4/1991 Laforge
5,052,407 A 10/1991 Hauser et al.
5,197,466 A 3/1993 Marchosky et al.
5,204,611 A 4/1993 Nor et al.
5,255,691 A 10/1993 Otten
5,257,634 A 11/1993 Kroll
5,342,408 A 8/1994 Decoriolis et al.
5,366,493 A 11/1994 Scheiner et al.
5,439,485 A 8/1995 Mar et al.
5,476,499 A 12/1995 Hirschberg
5,484,445 A 1/1996 Knuth
5,571,148 A 11/1996 Loeb et al.
5,592,070 A 1/1997 Mino
5,637,981 A 6/1997 Nagai et al.
5,676,162 A 10/1997 Larson, Jr. et al.
5,690,693 A 11/1997 Wang et al.
5,702,428 A 12/1997 Tippey et al.
5,702,431 A 12/1997 Wang et al.
5,712,795 A 1/1998 Layman et al.
5,713,939 A 2/1998 Nedungadi et al.
5,733,313 A 3/1998 Barreras, Sr. et al.
5,735,887 A 4/1998 Barreras, Sr. et al.
5,741,316 A 4/1998 Chen et al.
5,871,532 A 2/1999 Schroeppel
5,876,423 A 3/1999 Braun
5,902,331 A 5/1999 Bonner et al.
5,948,006 A 9/1999 Mann
5,949,632 A 9/1999 Barreras, Sr. et al.
5,957,965 A 9/1999 Moumane et al.
5,991,665 A 11/1999 Wang et al.
6,027,456 A 2/2000 Feler et al.
6,035,237 A 3/2000 Schulman et al.
6,052,624 A 4/2000 Mann
6,055,456 A 4/2000 Gerber
6,057,513 A 5/2000 Ushikoshi et al.
6,067,474 A 5/2000 Schulman et al.
6,075,339 A 6/2000 Reipur et al.
6,076,017 A 6/2000 Taylor et al.
6,081,097 A 6/2000 Seri et al.
6,083,247 A 7/2000 Rutten et al.
6,104,957 A 8/2000 Alo et al.
6,104,960 A 8/2000 Duysens et al.
6,138,681 A 10/2000 Chen et al.
6,165,180 A 12/2000 Cigaina et al.
6,166,518 A 12/2000 Echarri et al.
6,169,387 B1 1/2001 Kaib
6,172,556 B1 1/2001 Prentice
6,178,353 B1 1/2001 Griffith et al.
6,181,105 B1 1/2001 Cutolo et al.
6,191,365 B1 2/2001 Avellanet
6,208,894 B1 3/2001 Schulman et al.
6,212,430 B1 4/2001 Kung
6,212,431 B1 4/2001 Hahn et al.
6,221,513 B1 4/2001 Lasater
6,227,204 B1 5/2001 Baumann et al.
6,243,608 B1 6/2001 Pauly et al.
6,246,911 B1 6/2001 Seligman
6,249,703 B1 6/2001 Stanton et al.
6,265,789 B1 7/2001 Honda et al.
6,275,737 B1 8/2001 Mann
6,278,258 B1 8/2001 Echarri et al.
6,305,381 B1 10/2001 Weijand et al.
6,306,100 B1 10/2001 Prass
6,315,721 B2 11/2001 Schulman et al.
6,316,909 B1 11/2001 Honda et al.
6,321,118 B1 11/2001 Hahn
6,327,504 B1 12/2001 Dolgin et al.
6,354,991 B1 3/2002 Gross et al.
6,360,750 B1 3/2002 Gerber et al.
6,381,496 B1 4/2002 Meadows et al.
6,393,325 B1 5/2002 Mann et al.
6,438,423 B1 8/2002 Rezai et al.
6,442,434 B1 8/2002 Zarinetchi et al.
6,453,198 B1 9/2002 Torgerson et al.
6,466,817 B1 10/2002 Kaula et al.
6,473,652 B1 10/2002 Sarwal et al.
6,500,141 B1 12/2002 Irion
6,505,075 B1 1/2003 Weiner
6,505,077 B1 1/2003 Kast et al.
6,510,347 B2 1/2003 Borkan
6,516,227 B1 2/2003 Meadows et al.
6,517,227 B2 2/2003 Stidham et al.

(56) References Cited

U.S. PATENT DOCUMENTS 6,542,846 B1 4/2003 Miller et al.
6,553,263 B1 4/2003 Meadows et al.
6,584,355 B2 6/2003 Stessman
6,600,954 B2 7/2003 Cohen et al.
6,609,031 B1 8/2003 Law et al.
6,609,032 B1 8/2003 Woods et al.
6,609,945 B2 8/2003 Jimenez et al.
6,652,449 B1 11/2003 Gross et al.
6,662,051 B1 12/2003 Eraker et al.
6,664,763 B2 12/2003 Echarri et al.
6,685,638 B1 2/2004 Taylor et al.
6,721,603 B2 4/2004 Zabara et al.
6,735,474 B1 5/2004 Loeb et al.
6,745,077 B1 6/2004 Griffith et al.
6,792,314 B2 9/2004 Byers et al.
6,809,701 B2 10/2004 Amundson et al.
6,836,684 B1 12/2004 Rijkhoff et al.
6,847,849 B2 1/2005 Mamo et al.
6,892,098 B2 5/2005 Ayal et al.
6,895,280 B2 5/2005 Meadows et al.
6,896,651 B2 5/2005 Gross et al.
6,901,287 B2 5/2005 Davis et al.
6,941,171 B2 9/2005 Mann et al.
6,971,393 B1 12/2005 Mamo et al.
6,989,200 B2 1/2006 Byers et al.
6,990,376 B2 1/2006 Tanagho et al.
6,999,819 B2 2/2006 Swoyer et al.
7,051,419 B2 5/2006 Schrom et al.
7,054,689 B1 5/2006 Whitehurst et al.
7,069,081 B2 6/2006 Biggs et al.
7,127,298 B1 10/2006 He et al.
7,131,996 B2 11/2006 Wasserman et al.
7,142,925 B1 11/2006 Bhadra et al.
7,146,219 B2 12/2006 Sieracki et al.
7,151,914 B2 12/2006 Brewer
7,167,749 B2 1/2007 Biggs et al.
7,167,756 B1 1/2007 Torgerson et al.
7,177,690 B2 2/2007 Woods et al.
7,177,698 B2 2/2007 Klosterman et al.
7,181,286 B2 2/2007 Sieracki et al.
7,184,836 B1 2/2007 Meadows et al.
7,187,978 B2 3/2007 Malek et al.
7,191,005 B2 3/2007 Stessman
7,212,110 B1 5/2007 Martin et al.
7,225,028 B2 5/2007 Della Santina et al.
7,225,032 B2 5/2007 Schmeling et al.
7,231,254 B2 6/2007 DiLorenzo
7,234,853 B2 6/2007 Givoletti
7,239,918 B2 7/2007 Strother et al.
7,245,972 B2 7/2007 Davis
7,286,880 B2 10/2007 Olson et al.
7,295,878 B1 11/2007 Meadows et al.
7,305,268 B2 12/2007 Gliner et al.
7,317,948 B1 1/2008 King et al.
7,324,852 B2 1/2008 Barolat et al.
7,324,853 B2 1/2008 Ayal et al.
7,328,068 B2 2/2008 Spinelli et al.
7,330,764 B2 2/2008 Swoyer et al.
7,359,751 B1 4/2008 Erickson et al.
7,369,894 B2 5/2008 Gerber
7,386,348 B2 6/2008 North et al.
7,387,603 B2 6/2008 Gross et al.
7,396,265 B2 7/2008 Darley et al.
7,415,308 B2 8/2008 Gerber et al.
7,444,181 B2 10/2008 Shi et al.
7,444,184 B2 10/2008 Boveja et al.
7,450,991 B2 11/2008 Smith et al.
7,460,911 B2 12/2008 Cosendai et al.
7,463,928 B2 12/2008 Lee et al.
7,470,236 B1 12/2008 Kelleher et al.
7,483,752 B2 1/2009 Von Arx et al.
7,486,048 B2 2/2009 Tsukamoto et al.
7,496,404 B2 2/2009 Meadows et al.
7,515,967 B2 4/2009 Phillips et al.
7,532,936 B2 5/2009 Erickson et al.
7,539,538 B2 5/2009 Parramon et al.
7,551,960 B2 6/2009 Forsberg et al.
7,555,346 B1 6/2009 Woods et al.
7,565,203 B2 7/2009 Greenberg et al.
7,578,819 B2 8/2009 Bleich et al.
7,580,752 B2 8/2009 Gerber et al.
7,582,053 B2 9/2009 Gross et al.
7,617,002 B2 11/2009 Goetz
7,640,059 B2 12/2009 Forsberg et al.
7,643,880 B2 1/2010 Tanagho et al.
7,650,192 B2 1/2010 Wahlstrand
7,676,275 B1 3/2010 Farazi et al.
7,706,889 B2 4/2010 Gerber et al.
7,720,547 B2 5/2010 Denker et al.
7,725,191 B2 5/2010 Greenberg et al.
7,734,355 B2 6/2010 Cohen et al.
7,738,963 B2 6/2010 Hickman et al.
7,738,965 B2 6/2010 Phillips et al.
7,747,330 B2 6/2010 Nolan et al.
7,771,838 B1 8/2010 He et al.
7,774,069 B2 8/2010 Olson et al.
7,801,619 B2 9/2010 Gerber et al.
7,813,803 B2 10/2010 Heruth et al.
7,813,809 B2 10/2010 Strother et al.
7,826,901 B2 11/2010 Lee et al.
7,848,818 B2 12/2010 Barolat et al.
7,878,207 B2 2/2011 Goetz et al.
7,881,783 B2 2/2011 Bonde et al.
7,904,167 B2 3/2011 Klosterman et al.
7,912,555 B2 3/2011 Swoyer et al.
7,925,357 B2 4/2011 Phillips et al.
7,932,696 B2 4/2011 Peterson
7,933,656 B2 4/2011 Sieracki et al.
7,935,051 B2 5/2011 Miles et al.
7,937,158 B2 5/2011 Erickson et al.
7,952,349 B2 5/2011 Huang et al.
7,957,818 B2 6/2011 Swoyer
7,979,119 B2 7/2011 Kothandaraman et al.
7,979,126 B2 7/2011 Payne et al.
7,988,507 B2 8/2011 Darley et al.
8,000,782 B2 8/2011 Gharib et al.
8,000,800 B2 8/2011 Takeda et al.
8,000,805 B2 8/2011 Swoyer et al.
8,005,535 B2 8/2011 Gharib et al.
8,005,549 B2 8/2011 Boser et al.
8,005,550 B2 8/2011 Boser et al.
8,019,423 B2 9/2011 Possover
8,019,443 B2 9/2011 Schleicher et al.
8,024,047 B2 9/2011 Olson et al.
8,036,756 B2 10/2011 Swoyer et al.
8,044,635 B2 10/2011 Peterson
8,050,769 B2 11/2011 Gharib et al.
8,055,337 B2 11/2011 Moffitt et al.
8,068,912 B2 11/2011 Kaula et al.
8,083,663 B2 12/2011 Gross et al.
8,103,360 B2 1/2012 Foster
8,116,862 B2 2/2012 Stevenson et al.
8,121,701 B2 2/2012 Woods et al.
8,129,942 B2 3/2012 Park et al.
8,131,358 B2 3/2012 Moffitt et al.
8,140,168 B2 3/2012 Olson et al.
8,145,324 B1 3/2012 Stevenson et al.
8,150,530 B2 4/2012 Wesselink
8,175,717 B2 5/2012 Haller et al.
8,180,451 B2 5/2012 Hickman et al.
8,180,452 B2 5/2012 Shaquer
8,180,461 B2 5/2012 Mamo et al.
8,214,042 B2 7/2012 Ozawa et al.
8,214,048 B1 7/2012 Whitehurst et al.
8,214,051 B2 7/2012 Sieracki et al.
8,219,196 B2 7/2012 Torgerson
8,219,202 B2 7/2012 Giftakis et al.
8,224,460 B2 7/2012 Schleicher et al.
8,233,990 B2 7/2012 Goetz
8,255,057 B2 8/2012 Fang et al.
8,311,636 B2 11/2012 Gerber et al.
8,314,594 B2 11/2012 Scott et al.
8,332,040 B1 12/2012 Winstrom
8,340,786 B2 12/2012 Gross et al.

(56) References Cited

U.S. PATENT DOCUMENTS 8,362,742 B2 1/2013 Kallmyer
8,369,943 B2 2/2013 Shuros et al.
8,386,048 B2 2/2013 McClure et al.
8,417,346 B2 4/2013 Giftakis et al.
8,423,146 B2 4/2013 Giftakis et al.
8,447,402 B1 5/2013 Jiang et al.
8,447,408 B2 5/2013 North et al.
8,457,756 B2 6/2013 Rahman
8,457,758 B2 6/2013 Olson et al.
8,467,875 B2 6/2013 Bennett et al.
8,480,437 B2 7/2013 Dilmaghanian et al.
8,494,625 B2 7/2013 Hargrove
8,515,545 B2 8/2013 Trier
8,538,530 B1 9/2013 Orinski
8,543,223 B2 9/2013 Sage et al.
8,544,322 B2 10/2013 Minami et al.
8,549,015 B2 10/2013 Barolat
8,554,322 B2 10/2013 Olson et al.
8,555,894 B2 10/2013 Schulman et al.
8,562,539 B2 10/2013 Marino
8,571,677 B2 10/2013 Torgerson et al.
8,577,474 B2 11/2013 Rahman et al.
8,588,917 B2 11/2013 Whitehurst et al.
8,626,314 B2 1/2014 Swoyer et al.
8,644,933 B2 2/2014 Ozawa et al.
8,655,451 B2 2/2014 Klosterman et al.
8,700,175 B2 4/2014 Fell
8,706,254 B2 4/2014 Vamos et al.
8,725,262 B2 5/2014 Olson et al.
8,725,269 B2 5/2014 Nolan et al.
8,738,141 B2 5/2014 Smith et al.
8,738,148 B2 5/2014 Olson et al.
8,750,985 B2 6/2014 Parramon et al.
8,761,897 B2 6/2014 Kaula et al.
8,768,452 B2 7/2014 Gerber
8,774,912 B2 7/2014 Gerber
8,855,767 B2 10/2014 Faltys et al.
8,918,174 B2 12/2014 Woods et al.
8,954,148 B2 2/2015 Labbe et al.
8,989,861 B2 3/2015 Su et al.
9,044,592 B2 6/2015 Imran et al.
9,050,473 B2 6/2015 Woods et al.
9,089,712 B2 7/2015 Joshi et al.
9,108,063 B2 8/2015 Olson et al.
9,144,680 B2 9/2015 Kaula et al.
9,149,635 B2 10/2015 Denison et al.
9,155,885 B2 10/2015 Wei et al.
9,166,321 B2 10/2015 Smith et al.
9,168,374 B2 10/2015 Su
9,192,763 B2 11/2015 Gerber et al.
9,197,173 B2 11/2015 Denison et al.
9,199,075 B1 12/2015 Westlund
9,205,255 B2 12/2015 Strother et al.
9,209,634 B2 12/2015 Cottrill et al.
9,216,294 B2 12/2015 Bennett et al.
9,227,055 B2 1/2016 Wahlstrand et al.
9,227,076 B2 1/2016 Sharma et al.
9,238,135 B2 1/2016 Goetz et al.
9,240,630 B2 1/2016 Joshi
9,242,090 B2 1/2016 Atalar et al.
9,244,898 B2 1/2016 Vamos et al.
9,248,292 B2 2/2016 Trier et al.
9,259,578 B2 2/2016 Torgerson et al.
9,259,582 B2 2/2016 Joshi et al.
9,265,958 B2 2/2016 Joshi et al.
9,270,134 B2 2/2016 Gaddam et al.
9,272,140 B2 3/2016 Gerber et al.
9,283,394 B2 3/2016 Whitehurst et al.
9,295,851 B2 3/2016 Gordon et al.
9,308,022 B2 4/2016 Chitre et al.
9,308,382 B2 4/2016 Strother et al.
9,314,616 B2 4/2016 Wells et al.
9,320,899 B2 4/2016 Parramon et al.
9,333,339 B2 5/2016 Weiner
9,352,148 B2 5/2016 Stevenson et al.
9,352,150 B2 5/2016 Stevenson et al.
9,358,039 B2 6/2016 Kimmel et al.
9,364,658 B2 6/2016 Wechter
9,375,574 B2 6/2016 Kaula et al.
9,393,423 B2 7/2016 Parramon et al.
9,399,137 B2 7/2016 Parker et al.
9,409,020 B2 8/2016 Parker
9,415,211 B2 8/2016 Bradley et al.
9,427,571 B2 8/2016 Sage et al.
9,427,573 B2 8/2016 Gindele et al.
9,427,574 B2 8/2016 Lee et al.
9,433,783 B2 9/2016 Wei et al.
9,436,481 B2 9/2016 Drew
9,446,245 B2 9/2016 Grill et al.
9,463,324 B2 10/2016 Olson et al.
9,468,755 B2 10/2016 Westlund et al.
9,471,753 B2 10/2016 Kaula et al.
9,480,846 B2 11/2016 Strother et al.
9,492,672 B2 11/2016 Vamos et al.
9,492,675 B2 11/2016 Torgerson et al.
9,492,678 B2 11/2016 Chow
9,498,628 B2 11/2016 Kaemmerer et al.
9,502,754 B2 11/2016 Zhao et al.
9,504,830 B2 11/2016 Kaula et al.
9,522,282 B2 12/2016 Chow et al.
9,592,389 B2 3/2017 Moffitt
9,610,449 B2 4/2017 Kaula et al.
9,615,744 B2 4/2017 Denison et al.
9,623,257 B2 4/2017 Olson et al.
9,636,497 B2 5/2017 Bradley et al.
9,643,004 B2 5/2017 Gerber
9,653,935 B2 5/2017 Cong et al.
9,656,074 B2 5/2017 Simon et al.
9,656,076 B2 5/2017 Trier et al.
9,656,089 B2 5/2017 Yip et al.
9,675,809 B2 6/2017 Chow
9,687,649 B2 6/2017 Thacker
9,707,405 B2 7/2017 Shishilla et al.
9,713,706 B2 7/2017 Gerber
9,717,900 B2 8/2017 Swoyer et al.
9,724,526 B2 8/2017 Strother et al.
9,731,116 B2 8/2017 Chen
9,737,704 B2 8/2017 Wahlstrand et al.
9,744,347 B2 8/2017 Chen et al.
9,750,930 B2 9/2017 Chen
9,757,555 B2 9/2017 Novotny et al.
9,764,147 B2 9/2017 Torgerson
9,767,255 B2 9/2017 Kaula et al.
9,776,002 B2 10/2017 Parker et al.
9,776,006 B2 10/2017 Parker et al.
9,776,007 B2 10/2017 Kaula et al.
9,782,596 B2 10/2017 Vamos et al.
9,802,038 B2 10/2017 Lee et al.
9,814,884 B2 11/2017 Parker et al.
9,821,112 B2 11/2017 Olson et al.
9,827,415 B2 11/2017 Stevenson et al.
9,827,424 B2 11/2017 Kaula et al.
9,833,614 B1 12/2017 Gliner
9,849,278 B2 12/2017 Spinelli et al.
9,855,438 B2 1/2018 Parramon et al.
9,872,988 B2 1/2018 Kaula et al.
9,878,165 B2 1/2018 Wilder et al.
9,878,168 B2 1/2018 Shishilla et al.
9,882,420 B2 1/2018 Cong et al.
9,884,198 B2 2/2018 Parker
9,889,292 B2 2/2018 Gindele et al.
9,889,293 B2 2/2018 Siegel et al.
9,889,306 B2 2/2018 Stevenson et al.
9,895,532 B2 2/2018 Kaula et al.
9,899,778 B2 2/2018 Hanson et al.
9,901,284 B2 2/2018 Olsen et al.
9,901,740 B2 2/2018 Drees et al.
9,907,476 B2 3/2018 Bonde et al.
9,907,955 B2 3/2018 Bakker et al.
9,907,957 B2 3/2018 Woods et al.
9,924,904 B2 3/2018 Cong et al.
9,931,513 B2 4/2018 Kelsch et al.
9,931,514 B2 4/2018 Frysz et al.
9,950,171 B2 4/2018 Johanek et al.

(56) References Cited

U.S. PATENT DOCUMENTS 9,974,108 B2 5/2018 Polefko
9,974,949 B2 5/2018 Thompson et al.
9,981,121 B2 5/2018 Seifert et al.
9,981,137 B2 5/2018 Eiger
9,987,493 B2 6/2018 Torgerson et al.
9,993,650 B2 6/2018 Seitz et al.
9,999,765 B2 6/2018 Stevenson
10,004,910 B2 6/2018 Gadagkar et al.
10,016,596 B2 7/2018 Stevenson et al.
10,027,157 B2 7/2018 Labbe et al.
10,045,764 B2 8/2018 Scott et al.
10,046,164 B2 8/2018 Gerber
10,047,782 B2 8/2018 Sage et al.
10,052,490 B2 8/2018 Kaula et al.
10,065,044 B2 9/2018 Sharma et al.
10,071,247 B2 9/2018 Childs
10,076,661 B2 9/2018 Wei et al.
10,076,667 B2 9/2018 Kaula et al.
10,083,261 B2 9/2018 Kaula et al.
10,086,191 B2 10/2018 Bonde et al.
10,086,203 B2 10/2018 Kaemmerer
10,092,747 B2 10/2018 Sharma et al.
10,092,749 B2 10/2018 Stevenson et al.
10,095,837 B2 10/2018 Corey et al.
10,099,051 B2 10/2018 Stevenson et al.
10,103,559 B2 10/2018 Cottrill et al.
10,109,844 B2 10/2018 Dai et al.
10,118,037 B2 11/2018 Kaula et al.
10,124,164 B2 11/2018 Stevenson et al.
10,124,171 B2 11/2018 Kaula et al.
10,124,179 B2 11/2018 Norton et al.
10,141,545 B2 11/2018 Kraft et al.
10,173,062 B2 1/2019 Parker
10,179,241 B2 1/2019 Walker et al.
10,179,244 B2 1/2019 Lebaron et al.
10,183,162 B2 1/2019 Johnson et al.
10,188,857 B2 1/2019 North et al.
10,195,419 B2 2/2019 Shiroff et al.
10,206,710 B2 2/2019 Kern et al.
10,213,229 B2 2/2019 Chitre et al.
10,220,210 B2 3/2019 Walker et al.
10,226,617 B2 3/2019 Finley et al.
10,226,636 B2 3/2019 Gaddam et al.
10,236,709 B2 3/2019 Decker et al.
10,238,863 B2 3/2019 Gross et al.
10,238,877 B2 3/2019 Kaula et al.
10,244,956 B2 4/2019 Kane
10,245,434 B2 4/2019 Kaula et al.
10,258,800 B2 4/2019 Perryman et al.
10,265,532 B2 4/2019 Carcieri et al.
10,277,055 B2 4/2019 Peterson et al.
10,293,168 B2 5/2019 Bennett et al.
10,328,253 B2 6/2019 Wells
10,363,419 B2 7/2019 Simon et al.
10,369,275 B2 8/2019 Olson et al.
10,369,370 B2 8/2019 Shishilla et al.
10,376,701 B2 8/2019 Kaula et al.
10,448,889 B2 10/2019 Gerber et al.
10,456,574 B2 10/2019 Chen et al.
10,471,262 B2 11/2019 Perryman et al.
10,478,619 B2 11/2019 Lee et al.
10,485,970 B2 11/2019 Gerber et al.
10,493,282 B2 12/2019 Caparso et al.
10,493,287 B2 12/2019 Yoder et al.
10,561,835 B2 2/2020 Gerber
2002/0040185 A1 4/2002 Atalar et al.
2002/0051550 A1 5/2002 Leysieffer
2002/0051551 A1 5/2002 Leysieffer et al.
2002/0140399 A1 10/2002 Echarri et al.
2002/0156513 A1 10/2002 Borkan
2002/0177884 A1 11/2002 Ahn et al.
2003/0028231 A1 2/2003 Partridge et al.
2003/0114899 A1 6/2003 Woods et al.
2003/0212440 A1 11/2003 Boveja
2004/0087984 A1 5/2004 Kupiecki et al.
2004/0098068 A1 5/2004 Carbunaru et al.
2004/0172115 A1 9/2004 Miazga et al.
2004/0210290 A1 10/2004 Omar-Pasha
2004/0230282 A1 11/2004 Cates et al.
2004/0250820 A1 12/2004 Forsell
2004/0267137 A1 12/2004 Peszynski et al.
2005/0004619 A1 1/2005 Wahlstrand et al.
2005/0004621 A1 1/2005 Boveja et al.
2005/0021108 A1 1/2005 Klosterman et al.
2005/0075693 A1 4/2005 Toy et al.
2005/0075694 A1 4/2005 Schmeling et al.
2005/0075696 A1 4/2005 Forsberg et al.
2005/0075697 A1 4/2005 Olson et al.
2005/0075698 A1 4/2005 Phillips et al.
2005/0075699 A1 4/2005 Olson et al.
2005/0075700 A1 4/2005 Schommer et al.
2005/0104577 A1 5/2005 Matei et al.
2005/0187590 A1 8/2005 Boveja et al.
2006/0041295 A1 2/2006 Osypka
2006/0074412 A1 4/2006 Zerfas et al.
2006/0095078 A1 5/2006 Tronnes
2006/0142822 A1 6/2006 Tulgar
2006/0149345 A1 7/2006 Boggs et al.
2006/0200205 A1 9/2006 Haller
2006/0206166 A1 9/2006 Weiner
2007/0032836 A1 2/2007 Rope et al.
2007/0073295 A1* 3/2007 Biedermann ...... A61B 17/8685 606/62
2007/0239224 A1 10/2007 Bennett et al.
2007/0255368 A1 11/2007 Bonde et al.
2007/0255369 A1 11/2007 Bonde et al.
2007/0265675 A1 11/2007 Lund et al.
2007/0293914 A1 12/2007 Woods et al.
2008/0065182 A1 3/2008 Strother et al.
2008/0103570 A1 5/2008 Gerber
2008/0132969 A1 6/2008 Bennett et al.
2008/0154335 A1 6/2008 Rope et al.
2008/0161874 A1 7/2008 Bennett et al.
2008/0183236 A1 7/2008 Gerber
2008/0183257 A1 7/2008 Imran et al.
2009/0012592 A1* 1/2009 Buysman ................ A61N 1/05 607/116
2010/0076254 A1 3/2010 Jimenez et al.
2010/0076534 A1 3/2010 Mock
2010/0100158 A1 4/2010 Thrope et al.
2010/0160997 A1 6/2010 Johnson et al.
2010/0256696 A1 10/2010 Schleicher et al.
2011/0251662 A1 10/2011 Griswold et al.
2011/0257701 A1 10/2011 Strother et al.
2011/0270269 A1 11/2011 Swoyer et al.
2011/0282416 A1 11/2011 Hamann et al.
2011/0301663 A1 12/2011 Wang et al.
2011/0301667 A1 12/2011 Olson et al.
2011/0313427 A1 12/2011 Gindele et al.
2012/0041512 A1 2/2012 Weiner
2012/0046712 A1 2/2012 Woods et al.
2012/0053665 A1 3/2012 Stolz et al.
2012/0095478 A1 4/2012 Wang et al.
2012/0130448 A1 5/2012 Woods et al.
2012/0179221 A1 7/2012 Reddy et al.
2012/0191169 A1 7/2012 Rothstein et al.
2012/0203320 A1 8/2012 DiGiore et al.
2012/0232563 A1* 9/2012 Williams .......... A61M 25/0147 606/129
2012/0276854 A1 11/2012 Joshi et al.
2012/0276856 A1 11/2012 Joshi et al.
2012/0310317 A1 12/2012 Lund et al.
2012/0330354 A1 12/2012 Kane et al.
2013/0004925 A1 1/2013 Labbe et al.
2013/0006330 A1 1/2013 Wilder et al.
2013/0006331 A1 1/2013 Weisgarber et al.
2013/0018447 A1 1/2013 Ollivier et al.
2013/0023724 A1 1/2013 Allen et al.
2013/0131766 A1 5/2013 Crosby et al.
2013/0150925 A1 6/2013 Vamos et al.
2013/0150936 A1 6/2013 Takahashi
2013/0150939 A1 6/2013 Burnes et al.
2013/0184773 A1 7/2013 Libbus et al.
2013/0197608 A1 8/2013 Eiger

(56) References Cited

U.S. PATENT DOCUMENTS

| | | | | |
|---|---|---|---|---|
| 2013/0207863 | A1 | 8/2013 | Joshi | |
| 2013/0310894 | A1 | 11/2013 | Trier | |
| 2013/0331909 | A1 | 12/2013 | Gerber | |
| 2014/0046407 | A1 * | 2/2014 | Ben-Ezra | A61N 1/36114 607/62 |
| 2014/0128952 | A1 | 5/2014 | Jang et al. | |
| 2014/0222112 | A1 | 8/2014 | Fell | |
| 2014/0237806 | A1 | 8/2014 | Smith et al. | |
| 2014/0277270 | A1 | 9/2014 | Parramon et al. | |
| 2015/0088227 | A1 | 3/2015 | Shishilla et al. | |
| 2015/0214604 | A1 | 7/2015 | Zhao et al. | |
| 2017/0197079 | A1 | 7/2017 | Illegems et al. | |
| 2017/0340878 | A1 | 11/2017 | Wahlstrand et al. | |
| 2018/0021587 | A1 | 1/2018 | Strother et al. | |
| 2018/0036477 | A1 | 2/2018 | Olson et al. | |
| 2019/0269918 | A1 | 9/2019 | Parker | |
| 2019/0351244 | A1 | 11/2019 | Shishilla et al. | |
| 2019/0358395 | A1 | 11/2019 | Olson et al. | |

FOREIGN PATENT DOCUMENTS

| | | |
|---|---|---|
| AU | 5123800 | 11/2000 |
| CA | 2371378 | 11/2000 |
| CA | 2554676 | 9/2005 |
| CA | 2957962 | 5/2018 |
| CN | 101678203 | 3/2010 |
| CN | 102065947 | 5/2011 |
| CN | 103702713 | 4/2014 |
| DE | 3146182 | 6/1983 |
| EP | 0656218 | 6/1995 |
| EP | 1205004 | 5/2002 |
| EP | 1680182 | 7/2006 |
| EP | 2243509 | 10/2010 |
| EP | 1680182 | 5/2013 |
| ES | 2395128 | 2/2013 |
| HK | 1098715 | 3/2012 |
| JP | 06510209 | 11/1994 |
| JP | 2007268293 | 10/2007 |
| JP | 4125357 | 7/2008 |
| WO | 9820933 | 5/1998 |
| WO | 9918879 | 4/1999 |
| WO | 9934870 | 7/1999 |
| WO | 9942173 | 8/1999 |
| WO | 0027469 | 5/2000 |
| WO | 0056677 | 9/2000 |
| WO | 0065682 | 11/2000 |
| WO | 0069012 | 11/2000 |
| WO | 0183029 | 11/2001 |
| WO | 0209808 | 2/2002 |
| WO | 03084433 | 10/2003 |
| WO | 2004021876 | 3/2004 |
| WO | 2004103465 | 12/2004 |
| WO | 2005079295 | 9/2005 |
| WO | 2005081740 | 9/2005 |
| WO | 2006116205 | 11/2006 |
| WO | 2007022180 | 2/2007 |
| WO | 2008021524 | 2/2008 |
| WO | 2008094952 | 8/2008 |
| WO | 2008153726 | 12/2008 |
| WO | 2009102536 | 8/2009 |
| WO | 2009135075 | 11/2009 |
| WO | 2010107751 | 9/2010 |
| WO | 2011059565 | 5/2011 |
| WO | 2013063798 | 5/2013 |
| WO | 2013070490 | 5/2013 |
| WO | 2013156038 | 10/2013 |

OTHER PUBLICATIONS

"Bu-802a: How Does Rising Internal Resistance Affect Performance? Understanding the Importance of Low Conductivity", BatteryUniversity.com, Available Online at https://batteryuniversity.com/learn/article/rising_internal_resistance, Accessed from Internet on: May 15, 2020, 10 pages.

"DOE Handbook: Primer on Lead-Acid Storage Batteries", U.S. Dept. of Energy, Available Online at htt12s://www.stan dards.doe.gov/standards- documents/ I 000/1084-bhdbk-1995/@@images/file, Sep. 1995, 54 pages.

"Medical Electrical Equipment—Part 1: General Requirements for Safety", British Standard, BS EN 60601-1:1990-BS5724-1:1989, Mar. 1979, 200 pages.

"Summary of Safety and Effectiveness", Medtronic InterStim System for Urinary Control, Apr. 15, 1999, pp. 1-18.

"The Advanced Bionics PRECISION™ Spinal Cord Stimulator System", Advanced Bionics Corporation, Apr. 27, 2004, pp. 1-18.

"UL Standard for Safety for Medical and Dental Equipment", UL 544, 4th edition, Dec. 30, 1998, 128 pages.

Barnhart et al., "A Fixed-Rate Rechargeable Cardiac Pacemaker", APL Technical Digest, Jan.-Feb. 1970, pp. 2-9.

Benditt et al., "A Combined Atrial/Ventricular Lead for Permanent Dual-Chamber Cardiac Pacing Applications", Chest, vol. 83, No. 6, Jun. 1983, pp. 929-931.

Bosch et al., "Sacral (S3) Segmental Nerve Stimulation as a Treatment for Urge Incontinence in Patients with Detrusor Instability: Results of Chronic Electrical Stimulation Using an Implantable Neural Prosthesis", The Journal of Urology, vol. 154, No. 2, Aug. 1995, pp. 504-507.

Boyce et al., "Research Related to the Development of an Artificial Electrical Stimulator for the Paralyzed Human Bladder: a Review", The Journal of Urology, vol. 91, No. 1, Jan. 1964, pp. 41-51.

Bradley et al., "Further Experience With the Radio Transmitter Receiver Unit for the Neurogenic Bladder", Journal of Neurosurgery, vol. 20, No. 11, Nov. 1963, pp. 953-960.

Broggi et al., "Electrical Stimulation of the Gasserian Ganglion for Facial Pain: Preliminary Results", Acta Neurochirurgica, vol. 39, 1987, pp. 144-146.

Cameron et al., "Effects of Posture on Stimulation Parameters in Spinal Cord Stimulation", Neuromodulation, vol. 1, No. 4, Oct. 1998, pp. 177-183.

Chartier-Kastler , "Sacral Neuromodulation for Treating the Symptoms of Overactive Bladder Syndrome and Non-obstructive Urinary Retention:>10years of Clinical Experience", Journal Compilation, BJU international, vol. 101, 2007, pp. 417-423.

Connelly et al., "Atrial Pacing Leads Following Open Heart Surgery: Active or Passive Fixation?", Pacing and Clinical Electrophysiology, vol. 20, No. 10, Oct. 1997, pp. 2429-2433.

Fischell , "The Development of Implantable Medical Devices at the Applied Physics Laboratory", Johns Hopkins APL Technical Digest, vol. 13 No. 1, 1992, pp. 233-243.

Gaunt et al., "Control of Urinary Bladder Function With Devices: Successes and Failures", Progress in Brain Research, vol. 152, 2006, pp. 1-24.

Ghovanloo et al., "A Small Size Large Voltage Compliance Programmable Current Source for Biomedical Implantable Microstimulators", Proceedings of the 25th Annual International Conference of the IEEE EMBS, Sep. 17-21, 2003, pp. 1979-1982.

Helland , "Technical Improvements to be Achieved by the Year 2000: Leads and Connector Technology", Rate Adaptive Cardiac Pacing, Springer Verlag, 1993, pp. 279-292.

Hidefjall , "The Pace of Innovation-Patterns of Innovation in the Cardiac Pacemaker Industry", Linkoping University Press, 1997, 398 pages.

Ishihara et al., "A Comparative Study of Endocardial Pacemaker Leads", Cardiovascular Surgery, Nagoya Ekisaikai Hospital, 1st Dept. of Surgery, Nagoya University School of Medicine, 1981, pp. 132-135.

Jonas et al., "Studies on the Feasibility of Urinary Bladder Evacuation by Direct Spinal Cord Stimulation. I. Parameters of Most Effective Stimulation", Investigative urology, vol. 13, No. 2, 1975, pp. 142-150.

Kakuta et al., "In Vivo Long Lerm Evaluation of Transcutaneous Energy Lransmission for Lotally Implantable Artificial Heart", ASAIO Journal, Mar.-Apr. 2000, pp. 1-2.

(56) References Cited

OTHER PUBLICATIONS

Kesler et al., "Voltage-to-Frequency Converters", Available Online at: https://www.analog.com/media/cn/training-seminars/tutorials/ML-028.pdf, 7 pages.
Lazorthes et al., "Chronic Stimulation of the Gasserian Ganglion for Treatment of Atypical Facial Neuralgia", Pacing and Clinical Electrophysiology, vol. 10, Jan.-Feb. 1987, pp. 257-265.
Lewis et al., "Early Clinical Experience with the Rechargeable Cardiac Pacemaker", The Annals of Thoracic Surgery, vol. 18, No. 5, Nov. 1974, pp. 490-493.
Love et al., "Experimental Lesting of a Permanent Rechargeable Cardiac Pacemaker", The Annals of Thoracic Surgery, vol. 17, No. 2, Feb. 1, 1974, pp. 152-156.
Love , "Pacemaker Troubleshooting and Follow-up", Clinical Cardiac Pacing, Defibrillation, and Resynchronization Therapy, Chapter 24, 2007, pp. 1005-1062.
Madigan et al., "Difficulty of Extraction of Chronically Implanted Tined Ventricular Endocardial Leads", Journal of the American College of Cardiology, vol. 3, No. 3, Mar. 1984, pp. 724-731.
Meglio , "Percutaneously Implantable Chronic Electrode for Radiofrequency Stimulation of the Gasserian Ganglion. A Perspective in the Management of Trigeminal Pain", Acta Neurochirurgica, vol. 33, 1984, pp. 521-525.
Meyerson , "Alleviation of Atypical Trigeminal Pain by Stimulation of the Gasserian Ganglion via an Implanted Electrode", Acta Neurochirurgica Supplementum , vol. 30, 1980, pp. 303-309.
Mitamura et al., "Development of Transcutaneous Energy Transmission System", Available Online at https://www.researchgate.net/publication/312810915 Ch.28, Jan. 1988, pp. 265-270.
Nakamura et al., "Biocompatibility and Practicality Evaluations of Transcutaneous Energy Transmission Unit for the Totally Implantable Artifical Heart System", Journal of Artificial Organs, vol. 27, No. 2, 1998, pp. 347-351.
Nashold et al., "Electromicturition in Paraplegia. Implantation of a Spinal Neuroprosthesis", Arch Surg., vol. 104, Feb. 1972, pp. 195-202.
Painter et al., "Implantation of an Endocardial Tined Lead to Prevent Early Dislodgement", The Journal of Thoracic and Cardiovascular Surgery, vol. 77, No. 2, Feb. 1979, pp. 249-251.
Perez , "Lead-Acid Battery State of Charge vs. Voltage", Available Online at http://www.rencobattery.com/resources/SOC vs-Voltage.pdf, Aug.-Sep. 1993, 5 pages.
Schaldach et al., "A Long-Lived, Reliable, Rechargeable Cardiac Pacemaker", Engineering in Medicine, vol. 1: Advances in Pacemaker Technology, 1975, 34 pages.
Scheuer-Leeser et al., "Polyurethane Leads: Facts and Controversy", PACE, vol. 6, Mar.-Apr. 1983, pp. 454-458.
Smith , "Changing Standards for Medical Equipment", UL 544 and UL 187 vs. UL 2601 ("Smith"), 2002, 8 pages.
Tanagho et al., "Bladder Pacemaker: Scientific Basis and Clinical Future", Urology, vol. 20, No. 6, Dec. 1982, pp. 614-619.
Tanagho , "Neuromodulation and Neurostimulation: Overview and Future Potential", Translational Androl Urol, vol. 1, No. 1, 2012, pp. 44-49.
Torres et al., "Electrostatic Energy-Harvesting and Battery-Charging CMOS System Prototype", Available Online at http://rincon mora.gatech.edu/12ublicat/jrnls/tcasi09_hrv_sys.pdf, pp. 1-10.
Young , "Electrical Stimulation of the Trigeminal Nerve Root for the Treatment of Chronic Facial Pain", Journal of Neurosurgery, vol. 83, No. 1, Jul. 1995, pp. 72-78.
U.S. Appl. No. 14/827,081, filed Aug. 14, 2015.
U.S. Appl. No. 14/827,108, filed Aug. 14, 2015.
U.S. Appl. No. 14/991,752, filed Jan. 8, 2016.
U.S. Appl. No. 14/827,095, filed Aug. 14, 2015.
U.S. Appl. No. 14/827,067, filed Aug. 14, 2015.
U.S. Appl. No. 14/991,784, filed Jan. 8, 2016.
U.S. Appl. No. 62/101,888, filed Jan. 9, 2015.
U.S. Appl. No. 62/101,899, filed Jan. 9, 2015.
U.S. Appl. No. 62/041,611, filed Aug. 25, 2014.
U.S. Appl. No. 62/038,131, filed Aug. 15, 2014.
U.S. Appl. No. 62/101,897, filed Jan. 9, 2015.
U.S. Appl. No. 62/101,666, filed Jan. 9, 2015.
U.S. Appl. No. 62/101,884, filed Jan. 9, 2015.
U.S. Appl. No. 62/101,782, filed Jan. 9, 2015.
U.S. Appl. No. 62/191,134, filed Jul. 10, 2015.

* cited by examiner

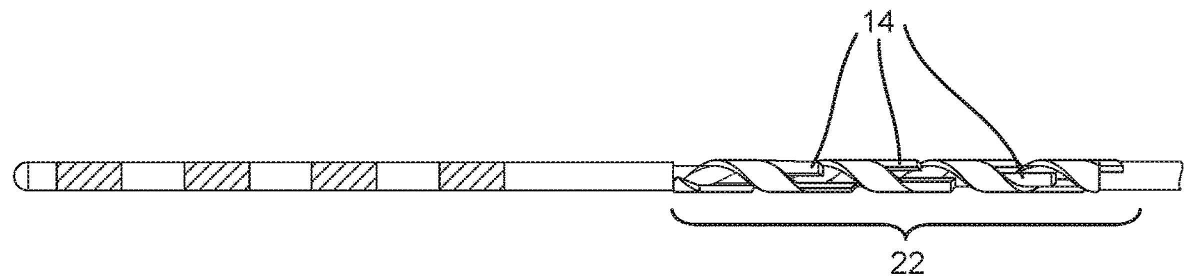
FIG. 9A
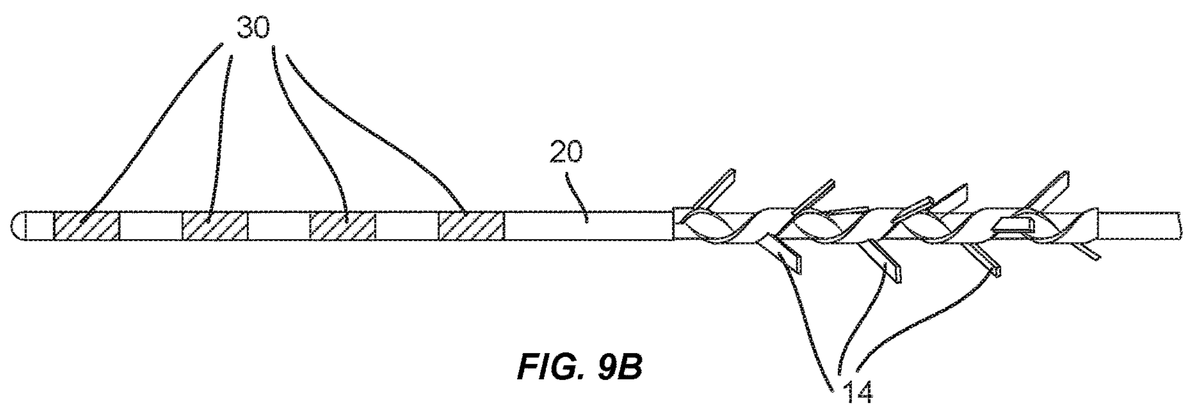
FIG. 9B
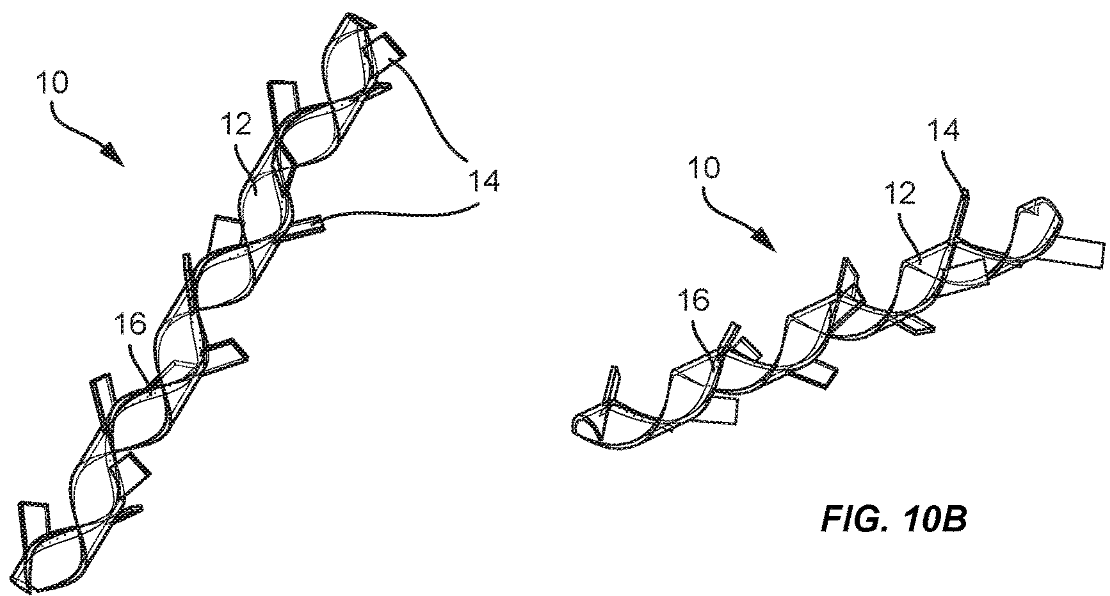
FIG. 10B
FIG. 10A

LASER CUT

RE-FLOW AFTER LASER CUT

IMPLANTABLE LEAD AFFIXATION STRUCTURE FOR NERVE STIMULATION TO ALLEVIATE BLADDER DYSFUNCTION AND OTHER INDICATION

CROSS-REFERENCES TO RELATED APPLICATIONS

The present application is a divisional of U.S. Non-Provisional application Ser. No. 15/719,487 filed on Sep. 28, 2017, which is a divisional of U.S. Non-Provisional application Ser. No. 14/827,074 filed on Aug. 14, 2015, which claims the benefit of priority of U.S. Provisional Application No. 62/038,122 filed on Aug. 15, 2014 and U.S. Provisional Application No. 62/110,274 filed on Jan. 30, 2015; each of which is incorporated herein by reference in its entirety.

The present application is also related to concurrently filed U.S. Non-Provisional patent application Ser. No. 14/827,081, entitled "External Pulse Generator Device and Associated Methods for Trial Nerve Stimulation;" U.S. Non-Provisional patent application Ser. No. 14/827,108, entitled "Electromyographic Lead Positioning and Stimulation Titration in a Nerve Stimulation System for Treatment of Overactive Bladder;" U.S. Non-Provisional patent application Ser. No. 14/827,095, entitled "Integrated Electromyographic Clinician Programmer For Use With an Implantable Neurostimulator;" and U.S. Non-Provisional patent application Ser. No. 14/827,067, entitled "Systems and Methods for Neurostimulation Electrode Configurations Based on Neural Localization;" and U.S. Provisional Application Nos. 62/101,666, entitled "Patient Remote and Associated Methods of Use With a Nerve Stimulation System" filed on Jan. 9, 2015; 62/101,884, entitled "Attachment Devices and Associated Methods of Use With a Nerve Stimulation Charging Device" filed on Jan. 9, 2015; 62/101,782, entitled "Improved Antenna and Methods of Use For an Implantable Nerve Stimulator" filed on Jan. 9, 2015; and 62/191,134, entitled "Implantable Nerve Stimulator Having Internal Electronics Without ASIC and Methods of Use" filed on Jul. 10, 2015; each of which is assigned to the same assignee and incorporated herein by reference in its entirety for all purposes.

FIELD OF THE INVENTION

The present invention relates to neurostimulation treatment systems and associated devices, as well as methods of treatment, implantation and configuration of such treatment systems.

BACKGROUND OF THE INVENTION

Treatments with implantable neurostimulation systems have become increasingly common in recent years. While such systems have shown promise in treating a number of conditions, effectiveness of treatment may vary considerably between patients. A number of factors may lead to the very different outcomes that patients experience, and viability of treatment can be difficult to determine before implantation. For example, stimulation systems often make use of an array of electrodes to treat one or more target nerve structures. The electrodes are often mounted together on a multi-electrode lead, and the lead implanted in tissue of the patient at a position that is intended to result in electrical coupling of the electrode to the target nerve structure, typically with at least a portion of the coupling being provided via intermediate tissues. Other approaches may also be employed, for example, with one or more electrodes attached to the skin overlying the target nerve structures, implanted in cuffs around a target nerve, or the like. Regardless, the physician will typically seek to establish an appropriate treatment protocol by varying the electrical stimulation that is applied to the electrodes.

Current stimulation electrode placement/implantation techniques and known treatment setting techniques suffer from significant disadvantages. The nerve tissue structures of different patients can be quite different, with the locations and branching of nerves that perform specific functions and/or enervate specific organs being challenging to accurately predict or identify. The electrical properties of the tissue structures surrounding a target nerve structure may also be quite different among different patients, and the neural response to stimulation may be markedly dissimilar, with an electrical stimulation pulse pattern, pulse width, frequency, and/or amplitude that is effective to affect a body function of one patient and potentially imposing significant discomfort or pain, or having limited effect, on another patient. Even in patients where implantation of a neurostimulation system provides effective treatment, frequent adjustments and changes to the stimulation protocol are often required before a suitable treatment program can be determined, often involving repeated office visits and significant discomfort for the patient before efficacy is achieved. While a number of complex and sophisticated lead structures and stimulation setting protocols have been implemented to seek to overcome these challenges, the variability in lead placement results, the clinician time to establish suitable stimulation signals, and the discomfort (and in cases the significant pain) that is imposed on the patient remain less than ideal. In addition, the lifetime and battery life of such devices is relatively short, such that implanted systems are routinely replaced every few years, which requires additional surgeries, patient discomfort, and significant costs to healthcare systems.

Furthermore, since the morphology of the nerve structures vary considerably between patients, placement and alignment of neurostimulation leads relative the targeted nerve structures can be difficult to control, which can lead to inconsistent placement, unpredictable results and widely varying patient outcomes. For these reasons, neurostimulation leads typically include multiple electrodes with the hope that at least one electrode or a pair of electrodes will be disposed in a location suitable for delivering neurostimulation. One drawback with this approach is that repeated office visits may be required to determine the appropriate electrodes to use and/or to arrive at a neurostimulation program that delivers effective treatment. Often, the number of usable neurostimulation programs may be limited by imprecise lead placement.

The tremendous benefits of these neural stimulation therapies have not yet been fully realized. Therefore, it is desirable to provide improved neurostimulation methods, systems and devices, as well as methods for implanting such neurostimulation systems for a particular patient or condition being treated. It would be particularly helpful to provide such systems and methods so as to improve ease of use by the physician in positioning and affixation of such leads to ensure proper lead placement is maintained after implantation so as to provide consistent and predictable results upon delivery of neurostimulation therapy. Therefore, it is desirable to provide methods and devices for implanting neurostimulation leads that improve anchoring of the lead and allow for reduced delivery profile of the lead during implantation.

BRIEF SUMMARY OF THE INVENTION

The present invention relates to implantable neurostimulation systems, and in particular to devices and methods for anchoring implanted neurostimulation leads. In one aspect, the invention includes an anchoring body extending helically about the lead and a plurality of tines disposed along the anchoring body. The plurality of tines are biased toward a deployed position in which the tines extend laterally outward from the helical body so as to engage tissue sufficiently to inhibit axial displacement of the implanted lead. The tines are constructed so as to be resiliently deflectable toward the helical body during implantation so as to fold inward toward the helical anchoring body when constrained by a delivery sheath to facilitate delivery to the target location during implantation.

In one aspect, a neurostimulation system in accordance with aspect of the invention includes an implantable lead having one or more conductors disposed within a lead body, the one or more conductors extending from a proximal end of the lead to one or more neurostimulation electrodes disposed at or near a distal end of the lead; a pulse generator coupleable to the proximal end of the implantable lead, the pulse generator being electrically coupled with the one or more neurostimulation electrodes when coupled to the implantable lead, the pulse generator being configured to generate a plurality of electrical impulses for delivering a neurostimulation treatment to a patient through the one or more neurostimulation electrodes when implanted at a target location; and an anchor coupled with the lead body just proximal of the electrodes.

In one aspect, the anchor includes a helical body extending helically on the outside of the lead body along a longitudinal axis thereof and a plurality of tines extending laterally away from the helical body. Each of the plurality of tines is biased to a deployed configuration and a delivery configuration. In the deployed configuration, the plurality of tines extend laterally away from longitudinal axis when the helical body is disposed thereon, and in the delivery configuration, the plurality of tines are folded inward toward the longitudinal axis of the lead body to facilitate delivery of the neurostimulation lead during implantation. In certain embodiments, the anchor is configured such that, in the delivery configuration, each of the plurality of tines is folded against the lead body so as to further reduce the delivery profile and, in the delivery configuration, the anchor has a cross-section or crossing profile compatible with a sheath having a diameter of 5 French or higher. In certain embodiments, the helical body and the plurality of tines are integrally formed of the same material, while in other embodiments the tines may be separate elements attached to the helical body. The tines are formed of a material with sufficient stiffness so that engagement of tissue with the plurality of tines inhibits axial movement of the lead when implanted in a tissue of the patient at the target location. In some embodiments, the anchor may be molded from a polyurethane based material having a shore hardness within a range between 50A and 80D. In other embodiments, the anchor may be formed of a metal, such as a shape-memory alloy. In still other embodiments, the anchor may be formed of a combination of materials, such as a polymer based material and a metal, such as a shape-memory alloy wire.

In certain embodiments, the anchor is dimensioned so that the helical body extends a length between 10 mm to 30 mm along the lead body when coupled thereon, preferably about 20 mm. Each of the plurality of tines may extend laterally outward from the longitudinal axis a distance between 1 mm to 4 mm. Each of the plurality of tines may be between 1.5 mm to 3 mm in length and between 0.5 mm to 2.0 mm in width. In some embodiments, the plurality of tines include tines of varying length, width and angle in the proximal direction, while in other embodiments, the plurality of tines may be of differing lengths or may angle in both proximal and distal directions. The plurality of tines may have a generally rectangular tab shape and may include rounded or chamfered corners and/or edges so as to inhibit tissue damage at the corners and/or edges. In some embodiments, the tines are biased toward an angle between 30 to 80 degrees from the longitudinal axis in the deployed configuration.

In one aspect, the helical body attaches to the lead body in an anchoring portion having a recessed portion with a reduced profile so as to further reduce the cross section, such as to 2 mm or less so as to accommodate a 5 French sheath for use in implanting the lead. In some embodiments, the anchor includes multiple anchor sections that may be attached to one another and deployed adjacent one another. This feature may allow the user to customize the anchoring portion as to both length and tine direction of the anchor, by reverse the anchors or combining differing types of anchors within the anchoring portion. The anchor may further include one or more additional features, including any of: a radiopaque element extending a substantial length of the helical body so as to facilitate positioning using visualization techniques; an embedded shield material suitable for shielding magnetic resonance induced heating; and biodegradable or drug eluting tines.

In certain embodiments, the helical body is a continuous helical flap and the plurality of tines comprise a plurality of sections of the continuous helical flap, the plurality of section defined by a plurality of cuts along a length of the continuous helical flap so as to allow the plurality of sections to fold inward without overlapping one another.

In other embodiments, the anchor is formed by laser cutting a tubular portion of a material (e.g. polymer or metal, such as Nitinol) and setting the material while the anchor is in the deployed configuration by heat setting or reflow. In still other embodiments, the anchor may be formed by injection molding a polymer material in a multi-piece mold assembly, which allows for further variability in the anchor structure, such as varying thicknesses in different portions of the anchor.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

FIGS. 9A-9B illustrate a neurostimulation lead with an anchor structure thereon before and after deployment, in accordance with aspects of the invention.

FIGS. 10A-10B illustrate an example anchor structure, in accordance with aspects of the invention.

DETAILED DESCRIPTION OF THE INVENTION

Figure 1:
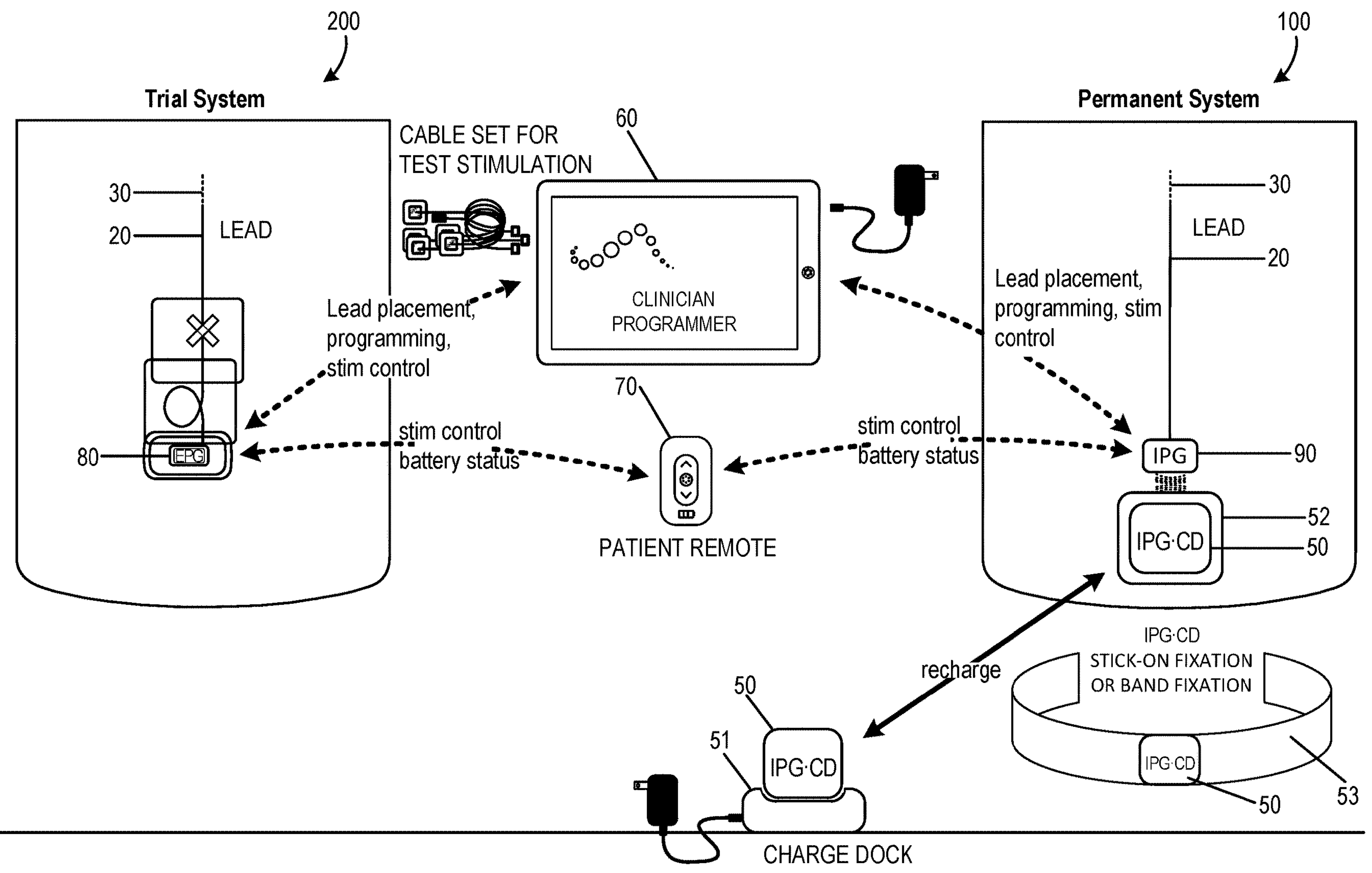
FIG. 1 schematically illustrates a nerve stimulation system, which includes a clinician programmer and a patient remote used in positioning and/or programming of both a trial neurostimulation system and a permanently implanted neurostimulation system, in accordance with aspects of the invention.

The present invention relates to neurostimulation treatment systems and associated devices, as well as methods of treatment, implantation/placement and configuration of such treatment systems. In particular embodiments, the invention relates to sacral nerve stimulation treatment systems configured to treat bladder dysfunctions, including overactive bladder ("OAB"), as well as fecal dysfunctions and relieve symptoms associated therewith. It will be appreciated however that the present invention may also be utilized for the treatment of pain or other indications, such as movement or affective disorders, as will be appreciated by one of skill in the art.

I. Neurostimulation Indications

Neurostimulation treatment systems, such as any of those described herein, can be used to treat a variety of ailments and associated symptoms, such as acute pain disorders, movement disorders, affective disorders, as well as bladder related dysfunction and bowel and fecal dysfunction. Examples of pain disorders that may be treated by neurostimulation include failed back surgery syndrome, reflex sympathetic dystrophy or complex regional pain syndrome, causalgia, arachnoiditis, and peripheral neuropathy. Movement orders include muscle paralysis, tremor, dystonia and Parkinson's disease. Affective disorders include depressions, obsessive-compulsive disorder, cluster headache, Tourette syndrome and certain types of chronic pain. Bladder related dysfunctions include but are not limited to OAB, urge incontinence, urgency-frequency, and urinary retention. OAB can include urge incontinence and urgency-frequency alone or in combination. Urge incontinence is the involuntary loss or urine associated with a sudden, strong desire to void (urgency). Urgency-frequency is the frequent, often uncontrollable urges to urinate (urgency) that often result in voiding in very small amounts (frequency). Urinary retention is the inability to empty the bladder. Neurostimulation treatments can be configured to address a particular condition by effecting neurostimulation of targeted nerve tissues relating to the sensory and/or motor control associated with that condition or associated symptom.

In one aspect, the methods and systems described herein are particularly suited for treatment of urinary and fecal dysfunctions. These conditions have been historically under-recognized and significantly underserved by the medical community. OAB is one of the most common urinary dysfunctions. It is a complex condition characterized by the presence of bothersome urinary symptoms, including urgency, frequency, nocturia and urge incontinence. It is estimated that about 40 million Americans suffer from OAB. Of the adult population, about 16% of all men and women live with OAB symptoms.

OAB symptoms can have a significant negative impact on the psychosocial functioning and the quality of life of patients. People with OAB often restrict activities and/or develop coping strategies. Furthermore, OAB imposes a significant financial burden on individuals, their families, and healthcare organizations. The prevalence of co-morbid conditions is also significantly higher for patients with OAB than in the general population. Co-morbidities may include falls and fractures, urinary tract infections, skin infections, vulvovaginitis, cardiovascular, and central nervous system pathologies. Chronic constipation, fecal incontinence, and overlapping chronic constipation occur more frequently in patients with OAB.

Conventional treatments of OAB generally include lifestyle modifications as a first course of action. Lifestyle modifications include eliminating bladder irritants (such as caffeine) from the diet, managing fluid intake, reducing weight, stopping smoking, and managing bowel regularity. Behavioral modifications include changing voiding habits (such as bladder training and delayed voiding), training pelvic floor muscles to improve strength and control of urethral sphincter, biofeedback and techniques for urge suppression. Medications are considered a second-line treatment for OAB. These include anti-cholinergic medications (oral, transdermal patch, and gel) and oral beta-3 adrenergic agonists. However, anti-cholinergics are frequently associated with bothersome, systemic side effects including dry mouth, constipation, urinary retention, blurred vision, somnolence, and confusion. Studies have found that more than 50% of patients stop using anti-cholinergic medications within 90 days due to a lack of benefit, adverse events, or cost.

When these approaches are unsuccessful, third-line treatment options suggested by the American Urological Association include intradetrusor (bladder smooth muscle) injections of botulinum toxin (BTX), Percutaneous Tibial Nerve Stimulation (PTNS) and Sacral Nerve Stimulation (SNM). BTX is administered via a series of intradetrusor injections under cystoscopic guidance, but repeat injections of BTX are generally required every 4 to 12 months to maintain effect and BTX may undesirably result in urinary retention. A number or randomized controlled studies have shown some efficacy of BTX injections in OAB patients, but long-term safety and effectiveness of BTX for OAB is largely unknown.

PTNS therapy consists of weekly, 30-minute sessions over a period of 12 weeks, each session using electrical stimulation that is delivered from a hand-held stimulator to the sacral plexus via the tibial nerve. For patients who respond well and continue treatment, ongoing sessions, typically every 3-4 weeks, are needed to maintain symptom reduction. There is potential for declining efficacy if patients fail to adhere to the treatment schedule. Efficacy of PTNS has been demonstrated in a few randomized-controlled studies, however, there is limited data on PTNS effectiveness beyond 3-years and PTNS is not recommended for patients seeking a cure for urge urinary incontinence (UUI) (e.g., 100% reduction in incontinence episodes) (EAU Guidelines).

II. Sacral Neuromodulation

SNM is an established therapy that provides a safe, effective, reversible, and long-lasting treatment option for the management of urge incontinence, urgency-frequency, and non-obstructive urinary retention. SNM therapy involves the use of mild electrical pulses to stimulate the sacral nerves located in the lower back. Electrodes are placed next to a sacral nerve, usually at the S3 level, by inserting the electrode leads into the corresponding foramen of the sacrum. The electrodes are inserted subcutaneously and are subsequently attached to an implantable pulse generator (IPG). The safety and effectiveness of SNM for the treatment of OAB, including durability at five years for both urge incontinence and urgency-frequency patients, is supported by multiple studies and is well-documented. SNM has also been approved to treat chronic fecal incontinence in patients who have failed or are not candidates for more conservative treatments.

A. Implantation of Sacral Neuromodulation System

Currently, SNM qualification has a trial phase, and is followed if successful by a permanent implant. The trial phase is a test stimulation period where the patient is allowed to evaluate whether the therapy is effective. Typically, there are two techniques that are utilized to perform the test stimulation. The first is an office-based procedure termed the Percutaneous Nerve Evaluation (PNE) and the other is a staged trial.

In the PNE, a foramen needle is typically used first to identify the optimal stimulation location, usually at the S3 level, and to evaluate the integrity of the sacral nerves. Motor and sensory responses are used to verify correct needle placement, as described in Table 1 below. A temporary stimulation lead (a unipolar electrode) is then placed near the sacral nerve under local anesthesia. This procedure can be performed in an office setting without fluoroscopy. The temporary lead is then connected to an external pulse generator (EPG) taped onto the skin of the patient during the trial phase. The stimulation level can be adjusted to provide an optimal comfort level for the particular patient. The patient will monitor his or her voiding for 3 to 7 days to see if there is any symptom improvement. The advantage of the PNE is that it is an incision free procedure that can be performed in the physician's office using local anesthesia. The disadvantage is that the temporary lead is not securely anchored in place and has the propensity to migrate away from the nerve with physical activity and thereby cause failure of the therapy. If a patient fails this trial test, the physician may still recommend the staged trial as described below. If the PNE trial is positive, the temporary trial lead is removed and a permanent quadri-polar tined lead is implanted along with an IPG under general anesthesia.

Figure 3A:
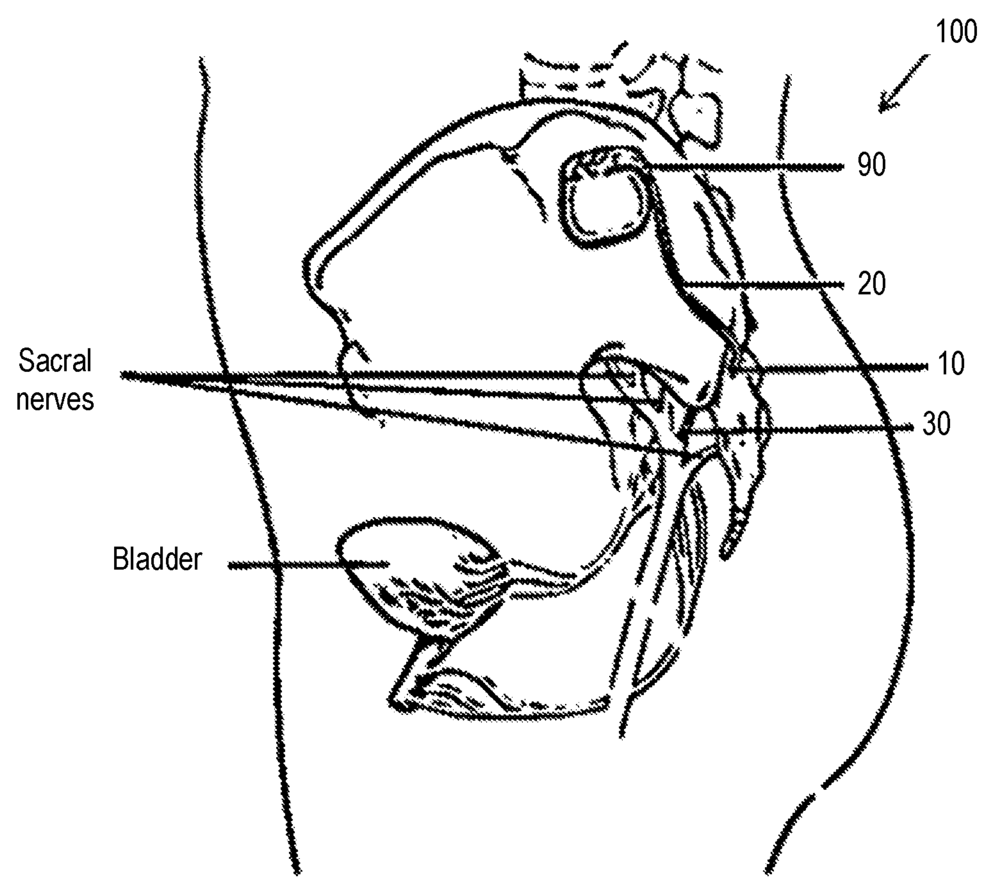
FIG. 3A shows an example of a fully implanted neurostimulation system in accordance with aspects of the invention.

A staged trial involves the implantation of the permanent quadri-polar tined stimulation lead into the patient from the start. It also requires the use of a foramen needle to identify the nerve and optimal stimulation location. The lead is implanted near the S3 sacral nerve and is connected to an EPG via a lead extension. This procedure is performed under fluoroscopic guidance in an operating room and under local or general anesthesia. The EPG is adjusted to provide an optimal comfort level for the patient and the patient monitors his or her voiding for up to two weeks. If the patient obtains meaningful symptom improvement, he or she is considered a suitable candidate for permanent implantation of the IPG under general anesthesia, typically in the upper buttock area, as shown in FIGS. 1 and 3A.

TABLE 1

Motor and Sensory Responses of SNM at Different Sacral Nerve Roots

| | Response | | |
|---|---|---|---|
| Nerve Innervation | Pelvic Floor | Foot/calf/leg | Sensation |
| S2 -Primary somatic contributor of pudendal nerve for external sphincter, leg, foot | "Clamp" * of anal sphincter | Leg/hip rotation, plantar flexion of entire foot, contraction of calf | Contraction of base of penis, vagina |
| S3 - Virtually all pelvic autonomic functions and striated mucle (levetor ani) | "bellows" ** of perineum | Plantar flexion of great toe, occasionally other toes | Pulling in rectum, extending forward to scrotum or labia |
| S4 - Pelvic autonomic and somatic; No leg pr foot | "bellows" ** | No lower extremity motor stimulation | Pulling in rectum only |

* Clamp: contraction of anal sphincter and, in males, retraction of base of penis. Move buttocks aside and look for anterior/posterior shortening of the perineal structures.
** Bellows: lifting and dropping of pelvic floor. Look for deepening and flattening of buttock groove In regard to measuring outcomes for SNM treatment of voiding dysfunction, the voiding dysfunction indications (e.g., urge incontinence, urgency-frequency, and non-obstructive urinary retention) are evaluated by unique primary voiding diary variables. The therapy outcomes are measured using these same variables. SNM therapy is considered successful if a minimum of 50% improvement occurs in any of primary voiding diary variables compared with the baseline. For urge incontinence patients, these voiding diary variables may include: number of leaking episodes per day, number of heavy leaking episodes per day, and number of pads used per day. For patients with urgency-frequency, primary voiding diary variables may include: number of voids per day, volume voided per void and degree of urgency experienced before each void. For patients with retention, primary voiding diary variables may include: catheterized volume per catheterization and number of catheterizations per day. For fecal incontinence patients, the outcome measures captured by the voiding diary include: number of leaking episodes per week, number of leaking days per week, and degree of urgency experienced before each leak.

The mechanism of action of SNM is multifactorial and impacts the neuro-axis at several different levels. In patients with OAB, it is believed that pudendal afferents can activate the inhibitory reflexes that promote bladder storage by inhibiting the afferent limb of an abnormal voiding reflex. This blocks input to the pontine micturition center, thereby restricting involuntary detrusor contractions without interfering with normal voiding patterns. For patients with urinary retention, SNM is believed to activate the pudendal nerve afferents originating from the pelvic organs into the spinal cord. At the level of the spinal cord, pudendal afferents may turn on voiding reflexes by suppressing exaggerated guarding reflexes, thus relieving symptoms of patients with urinary retention so normal voiding can be facilitated. In patients with fecal incontinence, it is hypothesized that SNM stimulates pudendal afferent somatic fibers that inhibit colonic propulsive activity and activates the internal anal sphincter, which in turn improves the symptoms of fecal incontinence patients.

The present invention relates to a system adapted to deliver neurostimulation to targeted nerve tissues in a manner that results in partial or complete activation of the target nerve fibers, causes the augmentation or inhibition of neural activity in nerves, potentially the same or different than the stimulation target, that control the organs and structures associated with bladder and bowel function.

B. EMG Assisted Neurostimulation Lead Placement and Programming

While conventional sacral nerve stimulation approaches have shown efficacy in treatment of bladder and bowel related dysfunctions, there exists a need to improve positioning of the neurostimulation leads and consistency between the trial and permanent implantation positions of the lead as well as to improve methods of programming. Neurostimulation relies on consistently delivering therapeutic stimulation from a pulse generator, via one or more neurostimulation electrodes, to particular nerves or targeted regions. The neurostimulation electrodes are provided on a distal end of an implantable lead that can be advanced through a tunnel formed in patient tissue. Implantable neurostimulation systems provide patients with great freedom and mobility, but it may be easier to adjust the neurostimulation electrodes of such systems before they are surgically implanted. It is desirable for the physician to confirm that the patient has desired motor and/or sensory responses before implanting an IPG. For at least some treatments (including treatments of at least some forms of urinary and/or fecal dysfunction), demonstrating appropriate motor responses may be highly beneficial for accurate and objective lead placement while the sensory response may not be required or not available (e.g., patient is under general anesthesia).

Placement and calibration of the neurostimulation electrodes and implantable leads sufficiently close to specific nerves can be beneficial for the efficacy of treatment. Accordingly, aspects and embodiments of the present disclosure are directed to aiding and refining the accuracy and precision of neurostimulation electrode placement. Further, aspects and embodiments of the present disclosure are directed to aiding and refining protocols for setting therapeutic treatment signal parameters for a stimulation program implemented through implanted neurostimulation electrodes.

Prior to implantation of the permanent device, patients may undergo an initial testing phase to estimate potential response to treatment. As discussed above, PNE may be done under local anesthesia, using a test needle to identify the appropriate sacral nerve(s) according to a subjective sensory response by the patient. Other testing procedures can involve a two-stage surgical procedure, where a quadripolar tined lead is implanted for a testing phase (Stage 1) to determine if patients show a sufficient reduction in symptom frequency, and if appropriate, proceeding to the permanent surgical implantation of a neuromodulation device. For testing phases and permanent implantation, determining the location of lead placement can be dependent on subjective qualitative analysis by either or both of a patient or a physician.

In exemplary embodiments, determination of whether or not an implantable lead and neurostimulation electrode is located in a desired or correct location can be accomplished through use of electromyography ("EMG"), also known as surface electromyography. EMG, is a technique that uses an EMG system or module to evaluate and record electrical activity produced by muscles, producing a record called an electromyogram. EMG detects the electrical potential generated by muscle cells when those cells are electrically or neurologically activated. The signals can be analyzed to detect activation level or recruitment order. EMG can be performed through the skin surface of a patient, intramuscularly or through electrodes disposed within a patient near target muscles, or using a combination of external and internal structures. When a muscle or nerve is stimulated by an electrode, EMG can be used to determine if the related muscle is activated, (i.e. whether the muscle fully contracts, partially contracts, or does not contract) in response to the stimulus. Accordingly, the degree of activation of a muscle can indicate whether an implantable lead or neurostimulation electrode is located in the desired or correct location on a patient. Further, the degree of activation of a muscle can indicate whether a neurostimulation electrode is providing a stimulus of sufficient strength, amplitude, frequency, or duration to affect a treatment regimen on a patient. Thus, use of EMG provides an objective and quantitative means by which to standardize placement of implantable leads and neurostimulation electrodes, reducing the subjective assessment of patient sensory responses.

In some approaches, positional titration procedures may optionally be based in part on a paresthesia or pain-based subjective response from a patient. In contrast, EMG triggers a measurable and discrete muscular reaction. As the efficacy of treatment often relies on precise placement of the neurostimulation electrodes at target tissue locations and the consistent, repeatable delivery of neurostimulation therapy, using an objective EMG measurement can substantially improve the utility and success of SNM treatment. The measurable muscular reaction can be a partial or a complete muscular contraction, including a response below the triggering of an observable motor response, such as those shown in Table 1, depending on the stimulation of the target muscle. In addition, by utilizing a trial system that allows the neurostimulation lead to remain implanted for use in the permanently implanted system, the efficacy and outcome of the permanently implanted system is more consistent with the results of the trial period, which moreover leads to improved patient outcomes.

C. Example System Embodiments

FIG. 1 schematically illustrates example nerve stimulation system setups, which includes a setup for use in a trial neurostimulation system 200 and a setup for use in a permanently implanted neurostimulation system 100, in accordance with aspects of the invention. The EPG 80 and IPG 50 are each compatible with and wirelessly communicate with a clinician programmer (CP) 60 and a patient remote 70, which are used in positioning and/or programming the trial neurostimulation system 200 and/or permanently implanted system 100 after a successful trial. As discussed above, the system utilizes a cable set and EMG sensor patches in the trial system setup 100 to facilitate lead placement and neurostimulation programming. CP can include specialized software, specialized hardware, and/or both, to aid in lead placement, programming, re-programming, stimulation control, and/or parameter setting. In addition, each of the IPG and the EPG allows the patient at least some control over stimulation (e.g., initiating a pre-set program, increasing or decreasing stimulation), and/or to monitor battery status with the patient remote. This approach also allows for an almost seamless transition between the trial system and the permanent system.

In one aspect, the CP 60 is used by a physician to adjust the settings of the EPG and/or IPG while the lead is implanted within the patient. The CP can be a tablet computer used by the clinician to program the IPG, or to control the EPG during the trial period. The CP can also include capability to record stimulation-induced electromyograms to facilitate lead placement and programming. The patient remote 70 can allow the patient to turn the stimulation on or off, or to vary stimulation from the IPG while implanted, or from the EPG during the trial phase.

In another aspect, the CP 60 has a control unit which can include a microprocessor and specialized computer-code instructions for implementing methods and systems for use by a physician in deploying the treatment system and setting up treatment parameters. The CP generally includes a graphical user interface, an EMG module, an EMG input that can couple to an EMG output stimulation cable, an EMG stimulation signal generator, and a stimulation power source. The stimulation cable can further be configured to couple to any or all of an access device (e.g., a foramen needle), a treatment lead of the system, or the like. The EMG input may be configured to be coupled with one or more sensory patch electrode(s) for attachment to the skin of the patient adjacent a muscle (e.g., a muscle enervated by a target nerve). Other connectors of the CP may be configured for coupling with an electrical ground or ground patch, an electrical pulse generator (e.g., an EPG or an IPG), or the like. As noted above, the CP can include a module with hardware and computer-code to execute EMG analysis, where the module can be a component of the control unit microprocessor, a pre-processing unit coupled to or in-line with the stimulation and/or sensory cables, or the like.

In other aspects, the CP 60 allows the clinician to read the impedance of each electrode contact whenever the lead is connected to an EPG, an IPG or a CP to ensure reliable connection is made and the lead is intact. This may be used as an initial step in both positioning the lead and in programming the leads to ensure the electrodes are properly functioning. The CP 60 is also able to save and display previous (e.g., up to the last four) programs that were used by a patient to help facilitate re-programming. In some embodiments, the CP 60 further includes a USB port for saving reports to a USB drive and a charging port. The CP is configured to operate in combination with an EPG when placing leads in a patient body as well with the IPG during programming. The CP can be electronically coupled to the EPG during test simulation through a specialized cable set or through wireless communication, thereby allowing the CP to configure, modify, or otherwise program the electrodes on the leads connected to the EPG. The CP may also include physical on/off buttons to turn the CP on and off and/or to turn stimulation on and off.

The electrical pulses generated by the EPG and IPG are delivered to one or more targeted nerves via one or more neurostimulation electrodes at or near a distal end of each of one or more leads. The leads can have a variety of shapes, can be a variety of sizes, and can be made from a variety of materials, which size, shape, and materials can be tailored to the specific treatment application. While in this embodiment, the lead is of a suitable size and length to extend from the IPG and through one of the foramen of the sacrum to a targeted sacral nerve, in various other applications, the leads may be, for example, implanted in a peripheral portion of the patient's body, such as in the arms or legs, and can be configured to deliver electrical pulses to the peripheral nerve such as may be used to relieve chronic pain. It is appreciated that the leads and/or the stimulation programs may vary according to the nerves being targeted.

Figure 2A:
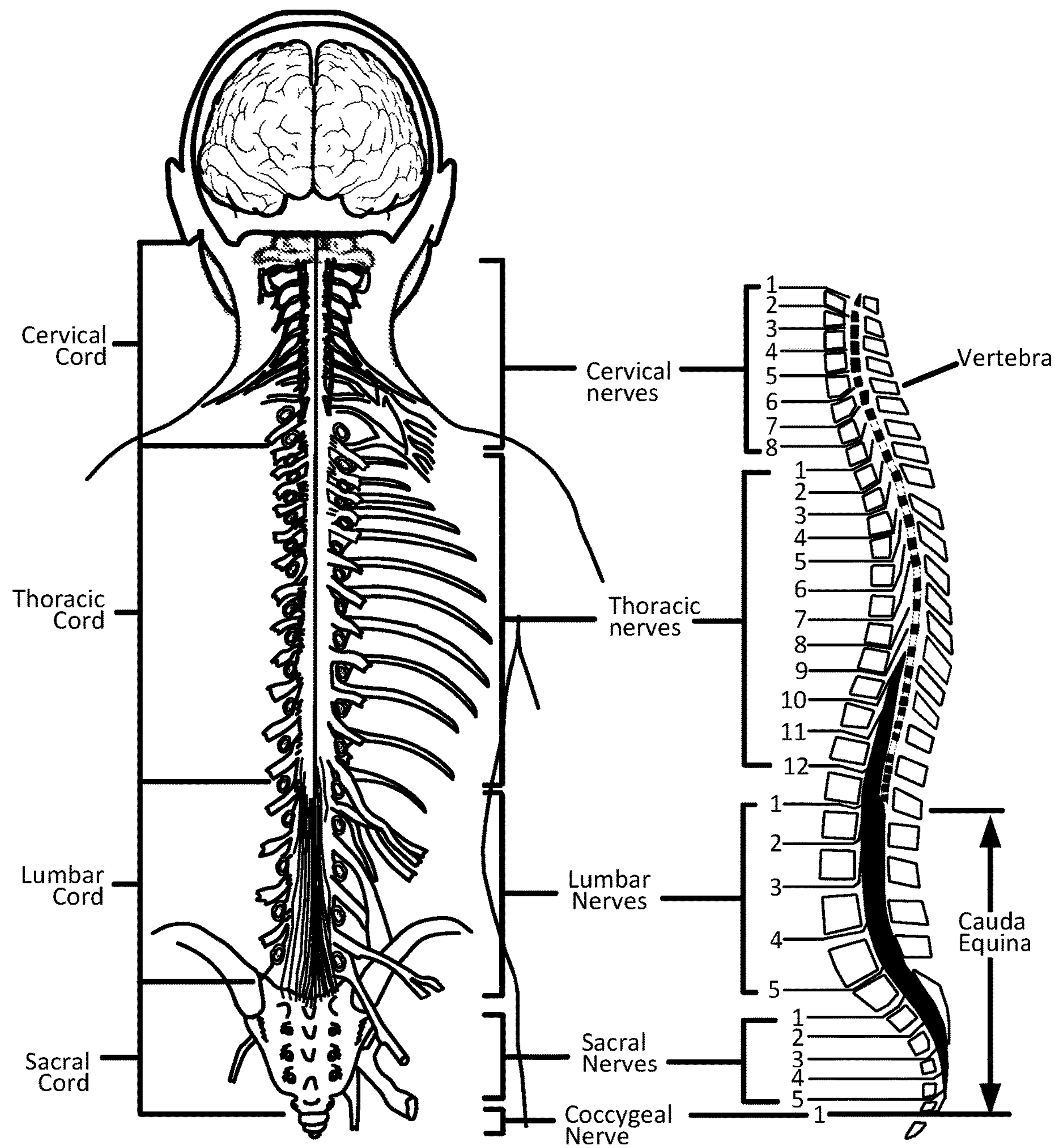
FIGS. 2A-2C show diagrams of the nerve structures along the spine, the lower back and sacrum region, which may be stimulated in accordance with aspects of the invention.
Figure 2B:
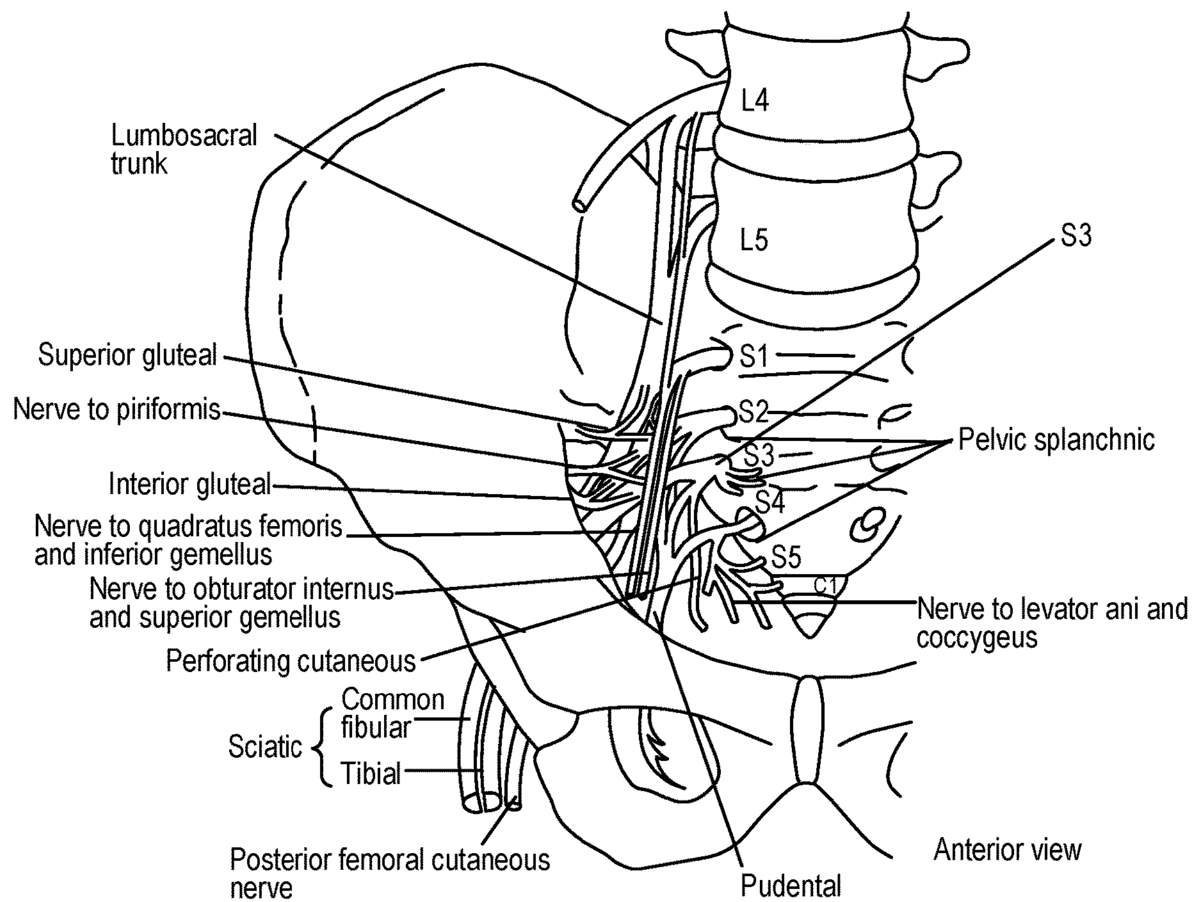
Figure 2C:
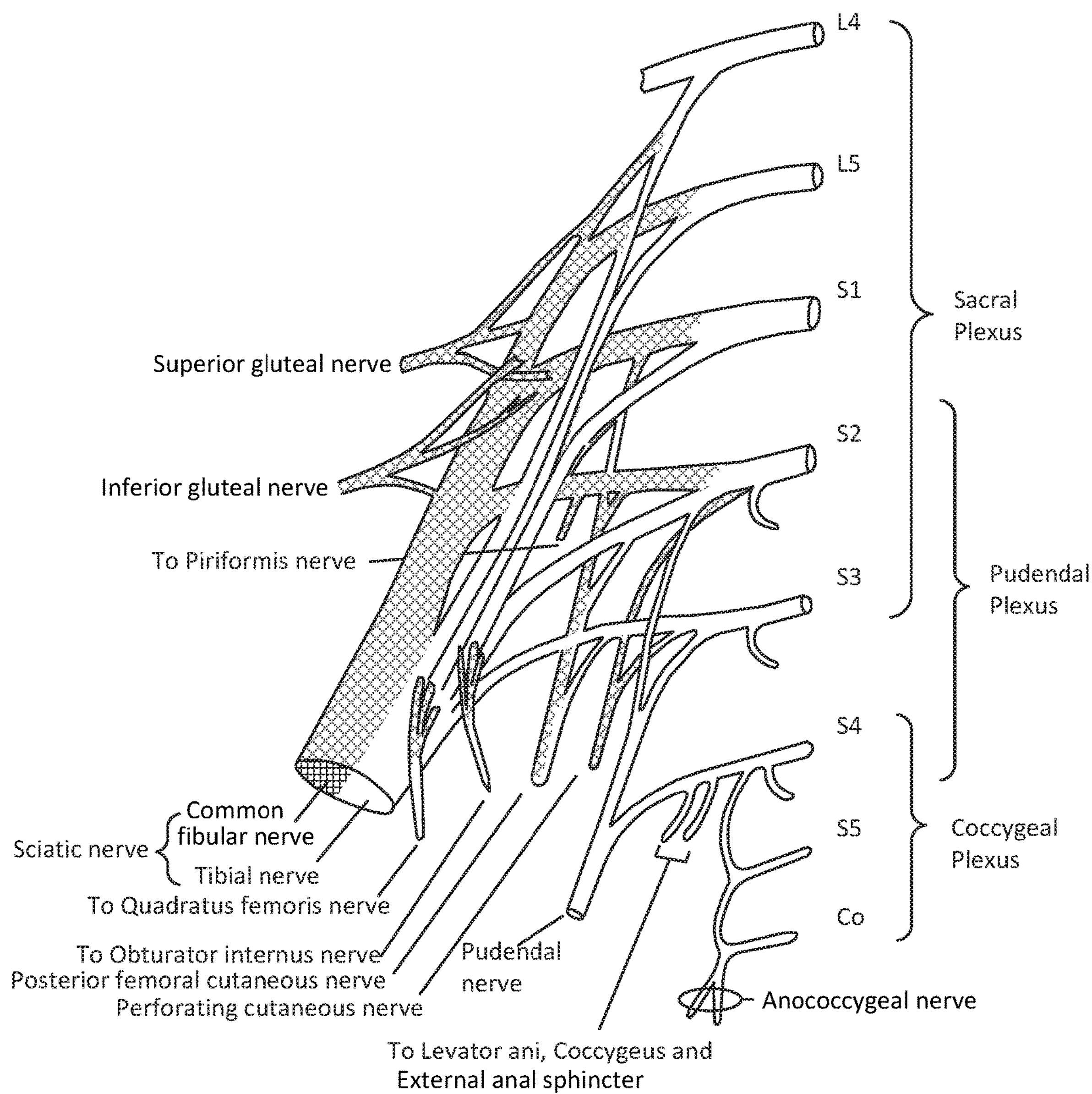

FIGS. 2A-2C show diagrams of various nerve structures of a patient, which may be used in neurostimulation treatments, in accordance with aspects of the invention. FIG. 2A shows the different sections of the spinal cord and the corresponding nerves within each section. The spinal cord is a long, thin bundle of nerves and support cells that extend from the brainstem along the cervical cord, through the thoracic cord and to the space between the first and second lumbar vertebra in the lumbar cord. Upon exiting the spinal cord, the nerve fibers split into multiple branches that innervate various muscles and organs transmitting impulses of sensation and control between the brain and the organs and muscles. Since certain nerves may include branches that innervate certain organs, such as the bladder, and branches that innervate certain muscles of the leg and foot, stimulation of the nerve at or near the nerve root near the spinal cord can stimulate the nerve branch that innervate the targeted organ, which may also result in muscle responses associated with the stimulation of the other nerve branch. Thus, by monitoring for certain muscle responses, such as those in Table 1, either visually, through the use of EMG as described herein or both, the physician can determine whether the targeted nerve is being stimulated. While stimulation at a certain level may evoke robust muscle responses visible to the naked eye, stimulation at a lower level (e.g. sub-threshold) may still provide activation of the nerve associated with the targeted organ while evoking no corresponding muscle response or a response only visible with EMG. In some embodiments, this low level stimulation also does not cause any paresthesia. This is advantageous as it allows for treatment of the condition by neurostimulation without otherwise causing patient discomfort, pain or undesired muscle responses.

FIG. 2B shows the nerves associated with the lower back section, in the lower lumbar cord region where the nerve bundles exit the spinal cord and travel through the sacral foramens of the sacrum. In some embodiments, the neurostimulation lead is advanced through the foramen until the neurostimulation electrodes are positioned at the anterior sacral nerve root, while the anchoring portion of the lead proximal of the stimulation electrodes are generally disposed dorsal of the sacral foramen through which the lead passes, so as to anchor the lead in position. FIG. 2C shows detail views of the nerves of the lumbosacral trunk and the sacral plexus, in particular, the S1-S5 nerves of the lower sacrum. The S3 sacral nerve is of particular interest for treatment of bladder related dysfunction, and in particular OAB.

FIG. 3A schematically illustrates an example of a fully implanted neurostimulation system 100 adapted for sacral nerve stimulation. Neurostimulation system 100 includes an IPG implanted in a lower back region and connected to a neurostimulation lead extending through the S3 foramen for stimulation of the S3 sacral nerve. The lead is anchored by a tined anchor portion 10 that maintains a position of a set of neurostimulation electrodes 30 along the targeted nerve, which in this example, is the anterior sacral nerve root S3 which enervates the bladder so as to provide therapy for various bladder related dysfunctions. While this embodiment is adapted for sacral nerve stimulation, it is appreciated that similar systems can be used in treating patients with, for example, chronic, severe, refractory neuropathic pain originating from peripheral nerves or various urinary dysfunctions or still further other indications. Implantable neurostimulation systems can be used to either stimulate a target peripheral nerve or the posterior epidural space of the spine.

Properties of the electrical pulses can be controlled via a controller of the implanted pulse generator. In some embodiments, these properties can include, for example, the frequency, amplitude, pattern, duration, or other aspects of the electrical pulses. These properties can include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In the embodiment depicted in FIG. 3A, the implantable neurostimulation system 100 includes a controller in the IPG having one or more pulse programs, plans, or patterns that may be pre-programmed or created as discussed above. In some embodiments, these same properties associated with the IPG may be used in an EPG of a partly implanted trial system used before implantation of the permanent neurostimulation system 100.

Figure 3B:
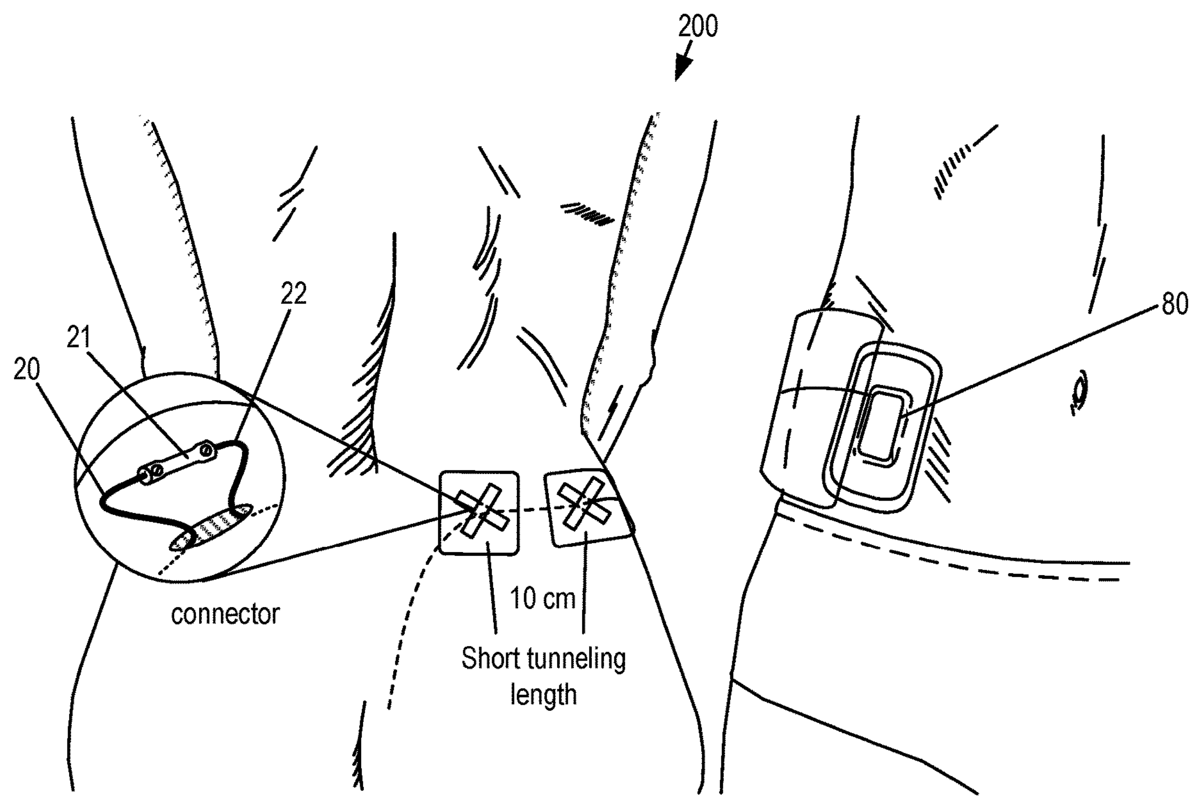
FIG. 3B shows an example of a neurostimulation system having a partly implanted stimulation lead and an external pulse generator adhered to the skin of the patient for use in a trial stimulation, in accordance with aspects of the invention.
Figure 3B:
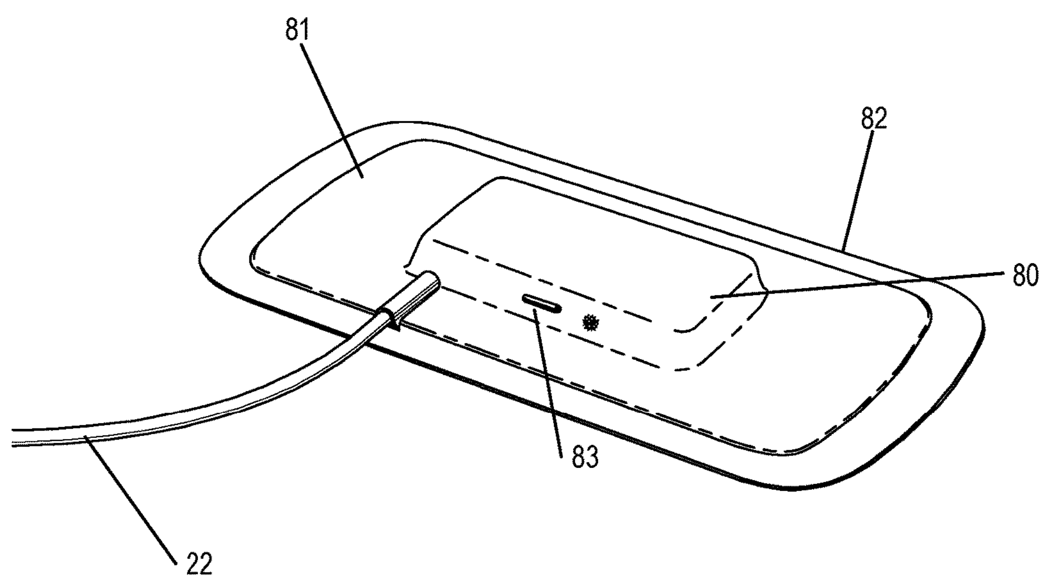

FIG. 3B shows a schematic illustration of a trial neurostimulation system 200 utilizing an EPG patch 81 adhered to the skin of a patient, particularly to the abdomen of a patient, the EPG 80 being encased within the patch. In one aspect, the lead is hardwired to the EPG, while in another the lead is removably coupled to the EPG through a port or aperture in the top surface of the flexible patch 81. Excess lead can be secured by an additional adherent patch. In one aspect, the EPG patch is disposable such that the lead can be disconnected and used in a permanently implanted system without removing the distal end of the lead from the target location. Alternatively, the entire system can be disposable and replaced with a permanent lead and IPG. When the lead of the trial system is implanted, an EMG obtained via the CP using one or more sensor patches can be used to ensure that the leads are placed at a location proximate to the target nerve or muscle, as discussed previously.

In some embodiments, the trial neurostimulation system utilizes an EPG 80 within an EPG patch 81 that is adhered to the skin of a patient and is coupled to the implanted neurostimulation lead 20 through a lead extension 22, which is coupled with the lead 20 through a connector 21. This extension and connector structure allows the lead to be extended so that the EPG patch can be placed on the abdomen and allows use of a lead having a length suitable for permanent implantation should the trial prove successful. This approach may utilize two percutaneous incisions, the connector provided in the first incision and the lead extensions extending through the second percutaneous incision, there being a short tunneling distance (e.g., about 10 cm) there between. This technique may also minimize movement of an implanted lead during conversion of the trial system to a permanently implanted system.

In one aspect, the EPG unit is wirelessly controlled by a patient remote and/or the CP in a similar or identical manner as the IPG of a permanently implanted system. The physician or patient may alter treatment provided by the EPG through use of such portable remotes or programmers and the treatments delivered are recorded on a memory of the programmer for use in determining a treatment suitable for use in a permanently implanted system. The CP can be used in lead placement, programming and/or stimulation control in each of the trial and permanent nerve stimulation systems. In addition, each nerve stimulation system allows the patient to control stimulation or monitor battery status with the patient remote. This configuration is advantageous as it allows for an almost seamless transition between the trial system and the permanent system. From the patient's viewpoint, the systems will operate in the same manner and be controlled in the same manner, such that the patient's subjective experience in using the trial system more closely matches what would be experienced in using the permanently implanted system. Thus, this configuration reduces any uncertainties the patient may have as to how the system will operate and be controlled such that the patient will be more likely to receive a trial system or a permanent system.

As shown in the detailed view of FIG. 3B, the EPG 80 is encased within a flexible laminated patch 81, which include an aperture or port through which the EPG 80 is connected to the lead extension 22. The patch may further an "on/off" button 83 with a molded tactile detail to allow the patient to turn the EPG on and/or off through the outside surface of the adherent patch 81. The underside of the patch 81 is covered with a skin-compatible adhesive 82 for continuous adhesion to a patient for the duration of the trial period. For example, a breathable strip having skin-compatible adhesive 82 would allow the EPG 80 to remain attached to the patient continuously during the trial, which may last over a week, typically two weeks to four weeks, or even longer.

While the above described systems provide considerable improvements in locating an optimal position of the lead and fine tuning lead placement and an optimal neurostimulation program is determined, it is imperative after the lead is successfully placed to ensure that the lead position is maintained over the course of therapy. Should the neurostimulation lead migrate, even a small axial distance, the electrodes may shift from the targeted nerve tissue such that the neurostimulation treatment may not delivery consistent results or no longer provide therapeutic effect without reprogramming or repositioning the lead.

In a fully implantable system, the pulse generator is implanted in the patient in an area having adequate size to comfortably contain the pulse generator, typically in a lower back region or lower abdominal region. Since the electrodes may need to be located a considerable distance from the implantable pulse generator, depending on the treatment or therapy being delivered, a neurostimulation lead is used to deliver the electrical pulses from the implanted pulse generator to the electrodes. While many such systems have proven effective, studies have shown that over time the neurostimulation lead may move, particularly when the lead extends through areas subject to movement. Such movement can dislocate the electrodes from the targeted location, such that the neurostimulation treatment becomes ineffective, requiring adjustment or replacement of the lead. Therefore, it is desirable to provide an anchoring device on the stimulation lead in such systems to inhibit movement of the lead and dislocation of the electrodes. While conventional neurostimulation has developed various anchoring mechanisms, such mechanisms often complicate the implantation procedure, undesirably increase the delivery profile of the lead, are difficult to replace or remove, or have proven ineffective.

Figure 4:
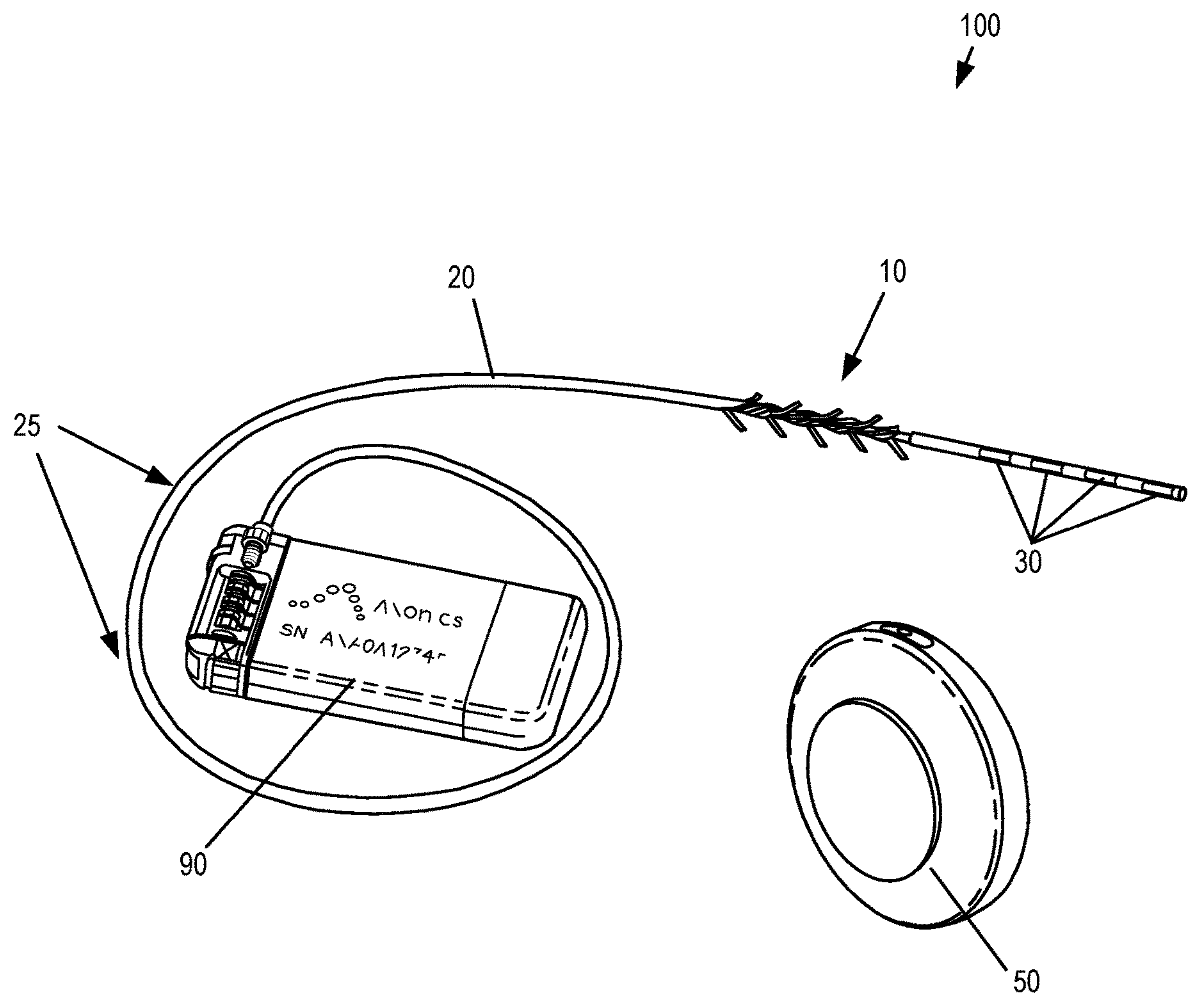
FIG. 4 shows an example of a neurostimulation system having an implantable stimulation lead, an implantable pulse generator, and an external charging device, in accordance with aspects of the invention.

FIG. 4 illustrates an example neurostimulation system 100 that is fully implantable and adapted for sacral nerve stimulation treatment. The implantable system 100 includes an IPG 90 that is coupled to a neurostimulation lead 20 that includes a group of neurostimulation electrodes 30 at a distal end of the lead. The lead includes a lead anchor portion 10 with a series of tines extending radially outward so as to anchor the lead and maintain a position of the neurostimulation lead 20 after implantation. The lead 20 may further include one or more radiopaque markers (e.g., silicon markers) 25 to assist in locating and positioning the lead using visualization techniques such as fluoroscopy. In some embodiments, the IPG provides monopolar or bipolar electrical pulses that are delivered to the targeted nerves through one or more neurostimulation electrodes. In sacral nerve stimulation, the lead is typically implanted through the S3 foramen as described herein.

As can be seen in FIG. 4, the neurostimulation lead 20 includes a plurality of neurostimulation electrodes 30 at a distal end of the lead and the anchor 10 is disposed just proximal of the electrodes 30. Typically, the anchor is disposed near and proximal of the plurality of electrodes so as to provide anchoring of the lead relatively close to the electrodes. This configuration is also advantageous as it allows for testing of the neurostimulation electrodes during implantation before deploying of the anchor (as described below), which allows the optimal location of the neurostimulation electrodes to be determined before the lead is anchored in place. As shown, the anchor 10 includes an anchor body 12 helically swept about the lead body and a plurality of tines 14 extending laterally outward from the helical body 12. This configuration is advantageous over conventional anchor devices as it provides a plurality of tines distributed both circumferentially and axially about the lead while extending from a common anchor body, thereby simplifying attachment and replacement of the anchoring tines. In addition, since the anchor body extends helically about the lead boy, this allows the flexibility of the lead body to be retained in the tined area. In one aspect, the anchor is constructed of a suitable material that is biocompatible as well as compatible with the material of which the lead body is formed and that is sufficiently flexible to provide anchoring force against the tissue without damaging the tissue.

Figure 5A:
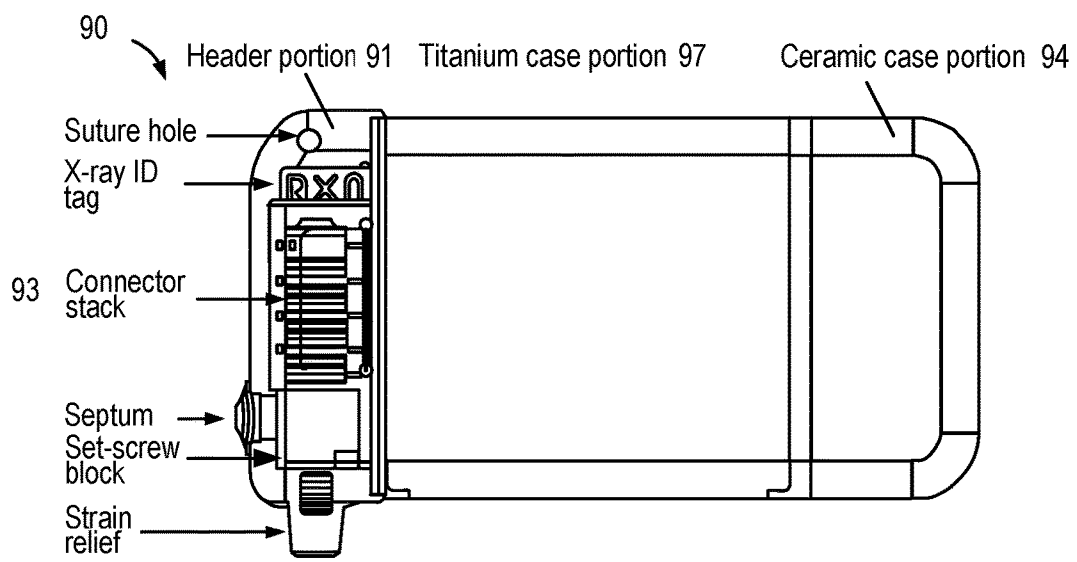
FIG. 5A-5C show detail views of an implantable pulse generator and associated components for use in a neurostimulation system, in accordance with aspects of the invention.
Figure 5B:
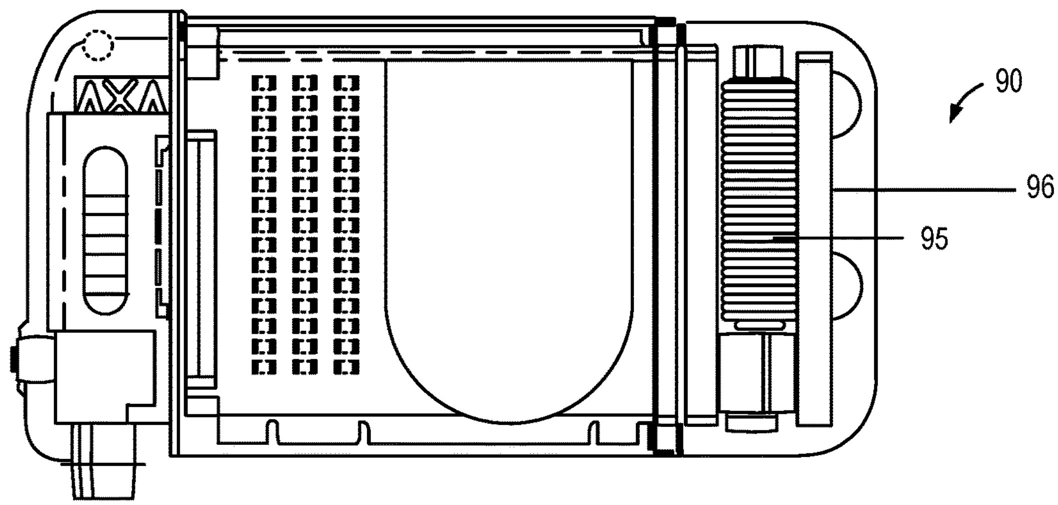
Figure 5C:
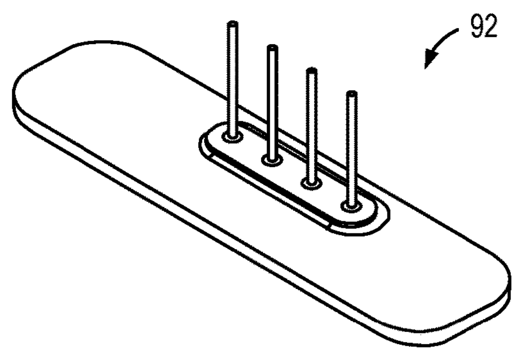

In one aspect, the IPG is rechargeable wirelessly through conductive coupling by use of a charging device 50 (CD), which is a portable device powered by a rechargeable battery to allow patient mobility while charging. The CD is used for transcutaneous charging of the IPG through RF induction. The CD can either be patched to the patient's skin using an adhesive or can be held in place using a belt 53 or by an adhesive patch 52, such as shown in the schematic of FIG. 1. The CD may be charged by plugging the CD directly into an outlet or by placing the CD in a charging dock or station 51 that connects to an AC wall outlet or other power source FIG. 5A-5C show detail views of the IPG and its internal components. In some embodiments, the pulse generator can generate one or more non-ablative electrical pulses that are delivered to a nerve to control pain or cause some other desired effect, for example to inhibit, prevent, or disrupt neural activity for the treatment of OAB or bladder related dysfunction. In some applications, the pulses having a pulse amplitude in a range between 0 mA to 1,000 mA, 0 mA to 100 mA, 0 mA to 50 mA, 0 mA to 25 mA, and/or any other or intermediate range of amplitudes may be used. One or more of the pulse generators can include a processor and/or memory adapted to provide instructions to and receive information from the other components of the implantable neurostimulation system. The processor can include a microprocessor, such as a commercially available microprocessor from Intel® or Advanced Micro Devices, Inc.®, or the like. An IPG may include an energy storage feature, such as one or more capacitors or a battery, one or more batteries, and typically includes a wireless charging unit.

One or more properties of the electrical pulses can be controlled via a controller of the IPG or EPG. In some embodiments, these properties can include, for example, the frequency, amplitude, pattern, duration, or other aspects of the timing and magnitude of the electrical pulses. These properties can further include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In one aspect, the IPG 90 includes a controller having one or more pulse programs, plans, or patterns that may be created and/or pre-programmed. In some embodiments, the IPG can be programmed to vary stimulation parameters including pulse amplitude in a range from 0 mA to 10 mA, pulse width in a range from 50 μs to 500 μs, pulse frequency in a range from 5 Hz to 250 Hz, stimulation modes (e.g., continuous or cycling), and electrode configuration (e.g., anode, cathode, or off), to achieve the optimal therapeutic outcome specific to the patient. In particular, this allows for an optimal setting to be determined for each patient even though each parameter may vary from person to person.

As shown in FIGS. 5A-5B, the IPG 90 may include a header portion 91 at one end and a ceramic portion 94 at the opposite end. The header portion 91 houses a feed through assembly 92 and connector stack 93, while the ceramic case portion 94 houses an antennae assembly 96 to facilitate wireless communication with the clinician program, the patient remote, and/or a charging coil to facilitate wireless charging with the CD. The remainder of the IPG is covered with a titanium case portion 97, which encases the printed circuit board, memory and controller components that facilitate the electrical pulse programs described above. In the example shown in FIG. 5C, the header portion of the IPG includes a four-pin feed-through assembly 92 that couples with the connector stack 93 in which the proximal end of the lead is coupled. The four pins correspond to the four electrodes of the neurostimulation lead. In some embodiments, a Balseal® connector block is electrically connected to four platinum/iridium alloy feed-through pins which are brazed to an alumina ceramic insulator plate along with a titanium alloy flange. This feed-through assembly is laser seam welded to a titanium-ceramic brazed case to form a complete hermetic housing for the electronics.

In the IPG shown in FIG. 5A, the ceramic and titanium brazed case is utilized on one end of the IPG where the ferrite coil and PCB antenna assemblies are positioned. A reliable hermetic seal is provided via a ceramic-to-metal brazing technique. The zirconia ceramic may comprise a 3Y-TZP (3 mol percent Yttria-stabilized tetragonal Zirconia Polycrystals) ceramic, which has a high flexural strength and impact resistance and has been commercially utilized in a number of implantable medical technologies. It will be appreciated, however, that other ceramics or other suitable materials may be used for construction of the IPG.

Utilization of ceramic material provides an efficient, radio-frequency-transparent window for wireless communication with the external patient remote and clinician's programmer as the communication antenna is housed inside the hermetic ceramic case. This ceramic window has further facilitated miniaturization of the implant while maintaining an efficient, radio-frequency-transparent window for long term and reliable wireless communication between the IPG and external controllers, such as the patient remote and CP. The IPG's wireless communication is generally stable over the lifetime of the device, unlike prior art products where the communication antenna is placed in the header outside the hermetic case. The communication reliability of such prior art devices tends to degrade due to the change in dielectric constant of the header material in the human body over time. The ferrite core is part of the charging coil assembly 95, shown in FIG. 5B, which is positioned inside the ceramic case 94. The ferrite core concentrates the magnetic field flux through the ceramic case as opposed to the metallic case portion 97. This configuration maximizes coupling efficiency, which reduces the required magnetic field and in turn reduces device heating during charging. In particular, because the magnetic field flux is oriented in a direction perpendicular to the smallest metallic cross section area, heating during charging is minimized. It is appreciated that these IPG structures and neurostimulation leads are described for illustrative purposes and that the anchoring structures described herein may be used with various other neurostimulation leads and IPGs in accordance with the principles of the invention.

The proximal end of the lead include a plurality of conductors corresponding to the plurality of electrodes at the distal end that electrically couple with corresponding contacts within the connector stack 93 within the header portion 91, thereby electrically connecting the IPG contacts with the neurostimulation electrodes 30 of the lead 20 for delivery of neurostimulation therapy. Although movement in the lower back region where the IPG is located is limited, the lead may still be subjected to forces and slight movement for various reasons, for example due to changes in tissue volume, trauma to the tissue region in which the system is implanted, or routine muscle movements. When these forces and movements are repeated over time, the connection between the proximal portion of the lead and the IPG may become compromised due to the fatigue caused by repeated stress and strain at the point of the stiffness mismatch that exists at the junction of the flexible lead and the IPG header portion 91. In some embodiments, a strain relief element that extends along a proximal portion of the lead where the lead exits the header portion 91 is included to provide strain relief at the junction of the proximal portion of the lead and the IPG so as to maintain integrity of the electrical connection and lengthen the useful life of the lead.

In some embodiments, the system includes a strain relief element that extends along a proximal portion of the lead adjacent the head portion of the IPG. The strain relief element may be disposed about the proximal portion of the lead or integrated into the lead itself. The strain relief element may include a proximal base that attaches or interfaces with a head portion of the IPG. In some embodiments, the strain relief element is a helical element that extends about the proximal portion of the lead. The strain relief element may be formed of a metal (e.g. stainless steel), polymer or any other suitable material. The proximal portion of the lead may include a recessed portion in which the strain relief element reside so that the outer surface of the strain relief element is substantially flush or about flush with the outer surface of the lead. Alternatively, the strain relief element may be applied to a non-recessed or standard sized portion anywhere along the lead body as needed. Typically, the strain relief element is a length within a range of about 1 inch to 6 inches so as to reduce flexing or bending of the proximal portion of the lead near the IPG, which can compromise the electrical connection over time. In one aspect, the strain relief element is formed so as to have an increased stiffness along a longitudinal axis so as to inhibit lateral bending of the proximal portion of the lead. Any of the aspects described herein in regard to the structure and design of the helical anchor body may be applicable to the strain relief element.

Figure 6A:
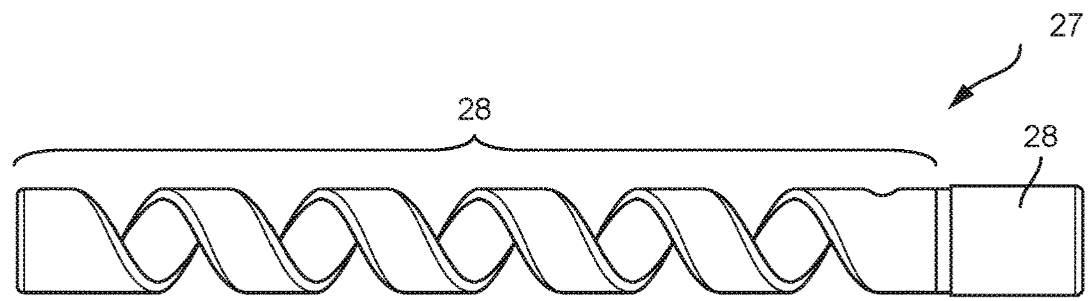
FIGS. 6A-6C show a strain relief structure for use with a neurostimulation lead and implantable pulse generator, in accordance with aspects of the invention.
Figure 6B:
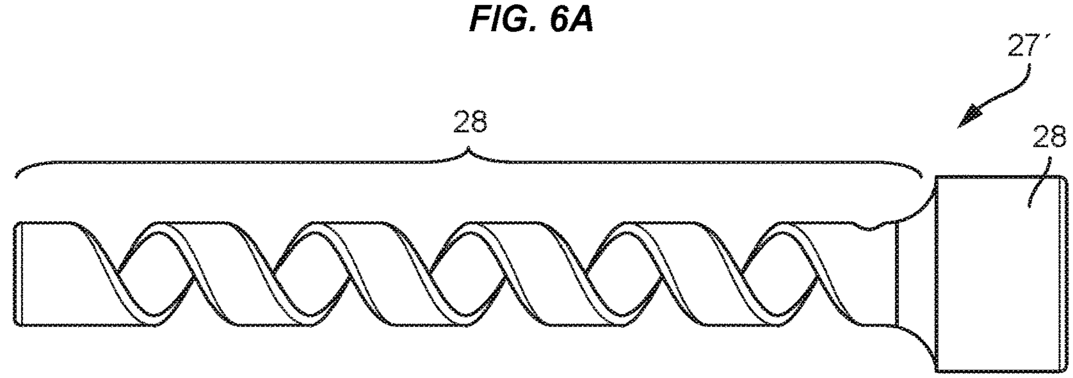
Figure 6C:
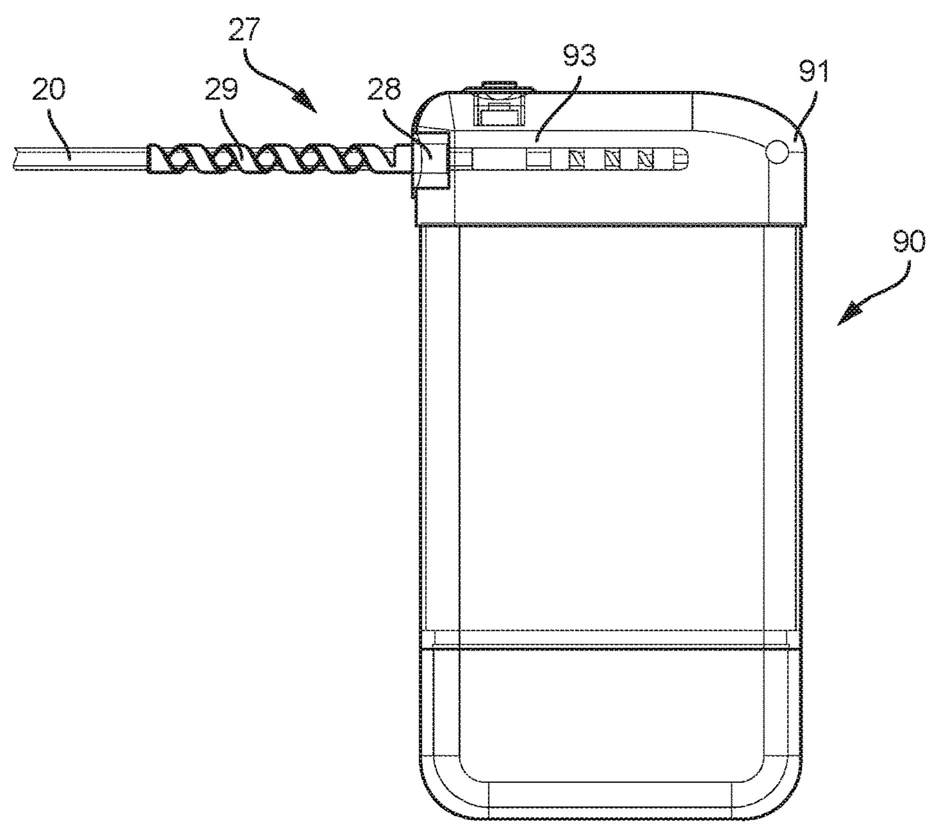

In some embodiments, the strain relief element 27 comprises a helical structure that extends along a proximal portion of the lead 20 adjacent where the lead 20 is inserted into the head portion 91 of the IPG 90, such as shown in FIG. 6C. The strain relief element 27 may include a proximal base 28 configured to securely attach to the header portion 91 and a helical portion 29 that encircles a proximal portion of the lead. Typically, the helical portion 29 exhibits increased stiffness as compared to the lead such that the helical portion 29 withstands any stresses or forces applied to the lead in the proximal region. Furthermore the helical structure limits the minimum bending radius in the region, which prevents sharp bends that can potentially damage the lead at the strain relief location. The strain relief element may be formed of any suitable, biocompatible material, including polymers or various metals (e.g. stainless steel, Nitinol). The strain relief member can be attached to the lead at manufacturing or alternatively, loaded onto the lead at the time of implant and attachment to the IPG connector.

In one aspect, the strain relief element is sufficiently thin such that its low profile does not substantially increase the maximum cross-section or crossing profile of the lead through the sheath. In some embodiments, the proximal portion of the lead may have a reduced diameter and dimension so as to fittingly receive the strain relief member so that the strain relief member is substantially flush with the outer surface of the lead distal of the strain relief member.

FIGS. 6A-6B illustrate detail views of example strain relief members 27 and 27', respectively, each including a proximal base 28 for securing to the IPG header portion and a helical strain relief portion 29 for wrapping about the proximal portion of the lead 20. The proximal base portion 28 may be sized and dimensioned according to a particular IPG header portion. In one aspect, the helical portions 29 can be configured to provide variable stiffness along the length of the proximal portion of the lead. For example, the helical portions 29 can be of variable thickness along the length of the strain relief to provide gradual stiffness transition in the region and/or the helical portions can vary in pitch and/or width along the length of the strain relief to provide gradual stiffness and limit the bend radius in the region. In another aspect, the strain relief element 27 can include one or more tines (not shown), similar to the anchors described herein, so as to provide tissue fixation to the strain relief portion and further inhibit movement or migration of the proximal portion of the lead.

III. Lead Affixation by Helical Anchors

Figure 7:
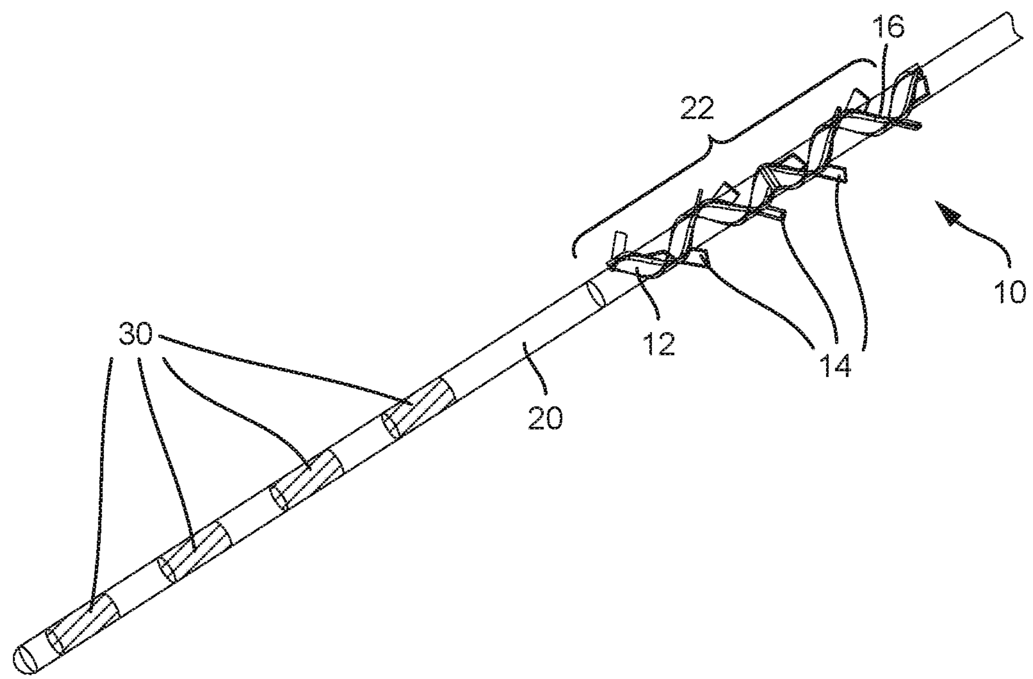
FIG. 7 illustrates a neurostimulation lead with an anchor structure thereon, in accordance with aspects of the invention.

FIG. 7 illustrates a detail view of a neurostimulation lead 20, similar to that in FIG. 4, with an anchoring body 10 mounted on an anchoring portion 22 of the lead, shown in the deployed configuration. As can be seen, the helical body 12 is helically swept about a central longitudinal axis for placement on the lead body and the plurality of tines 14 are distributed along the helical body 12 extending laterally outward from the central axis and angled in a proximal direction. As shown in the detail view of 10 FIG. 8, the plurality of tines 14 of the anchoring body are distributed so as to be radially offset from one another at regular intervals (e.g. 30°, 45°, 90°) within a range of intervals, such as between 10° and 90°, so that the plurality of tines extend outward in different directions circumferentially about the central axis. This distributes any anchoring forces about the lead body so as to improve anchoring of the lead.

In one aspect, the anchor 10 includes a radiopaque strip 16 embedded within the helical body 12 to allow localization of the anchor 10 through visualization techniques. The radiopaque strip may be fabricated from any radiopaque material, such as a platinum alloy (e.g. Pt/lr), so as to visible using standard visualization techniques. Such a strip is advantageous as it facilitates positioning of the lead at the targeted location. In other embodiments, the helical body may be formed of a material that is radiopaque, for example a radiopaque material may be blended into a polymer material of which the anchor is formed.

FIGS. 9A-9B illustrate a neurostimulation lead having an attached anchor in a delivery configuration and a deployed configuration, respectively. In FIG. 9A, the plurality of tines 14 are folded against the body of the lead 20 without overlapping each other or an adjacent section of the helical body. Typically, the tines are constrained in the delivery configuration by an outer sheath (not shown) while the lead is advanced through a tunnel in a tissue to the targeted location. The helical body is swept at a pitch to allow sufficient space between adjacent turns of the helical body for a tab to fold inward against the lead boy, which allows for a reduced delivery profile. In one aspect, the cross section of the anchor is less than 2.0 mm, sufficiently small to be delivered through a 5 French sheath. In one aspect, the lead body includes a recessed portion 22 having a reduced outer diameter, in which the helical body 12 is attached. This feature facilitates coupling between the anchor 10 and the lead body 20 as the proximal and distal ends of the anchor abut against the proximal and distal ends of the recessed portion and allow for a reduced cross-section or crossing profile of the anchor portion of the lead. Once delivery of the electrodes to the target location is confirmed, the sheath may be withdrawn proximally, thereby allowing the plurality of tines to resiliently return to the deployed configuration toward which they are biased, as shown in FIG. 9B.

FIGS. 10A-10B illustrate detail views of the anchor 10 shown in FIG. 9B in the deployed configuration. In this embodiment, the tines 14 are all inclined proximally. It is understood, however, that in other embodiments, the anchor 10 may be configured so that the tines are angled distally or proximally, extend perpendicular to the longitudinal axis of the helical body, or extend in multiple differing directions as desired for a particular application.

In one aspect, the anchor is fabricated from a material sufficiently stiff to exert adequate anchoring forces to maintain the lead in place, yet sufficiently flexibly to fold inward against the lead and to avoid damaging tissue should the lead be removed from the tissue. In some embodiments, the anchor is fabricated from a molded polyurethane having a shore hardness within a range between 50A and 80D, preferably about 70D. The helical body may have a width between 1.0 mm to 3.0 mm, preferably about 2.0 mm and a total length between 10 mm and 30 mm, preferably about 20 mm. The anchor is configured such that the crossing profile is less than 2.0 mm, preferably 1.7 mm or less, so that a lead having the anchor attached thereto can be delivered through a standard sheath, such as a 5 French sheath. In certain embodiments, the tines have a length between 1 mm and 3 mm, preferably about 1.8 mm; a width between 0.5 and 2.0 mm, preferably about 0.8 mm; and a thickness between 0.2 mm and 0.5 mm, preferably about 0.3 mm. In certain embodiments, the anchor includes between 10 and 20 tines, preferably about 12 to 16 tines, spaced apart along the length of the helical body so as to extend in different directions circumferentially about the lead. In some embodiments, the tines are all of the same length and angle in the same direction, while in other embodiments, the tines may be of varying lengths, widths and may angle in both proximal and distal directions. While it is advantageous to dimension any of the anchor described herein according to the above described configuration in order to facilitate delivery of the anchor through a 5 French sheath, it is appreciated that the anchor may be configured according to various other dimensions (length, number of tines, etc.) as desired for a particular application or neurostimulation lead.

Figure 8:
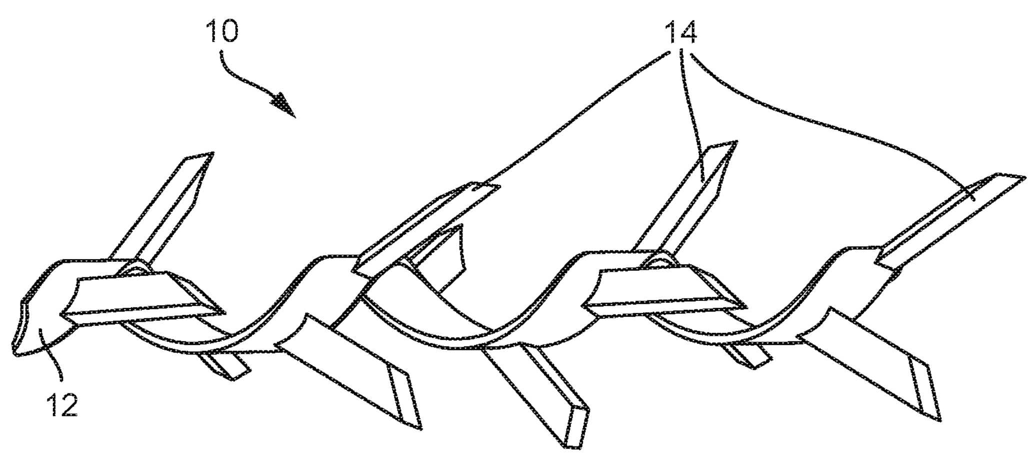
FIG. 8 illustrates an example anchor structure, in accordance with aspects of the invention.
Figure 11A:
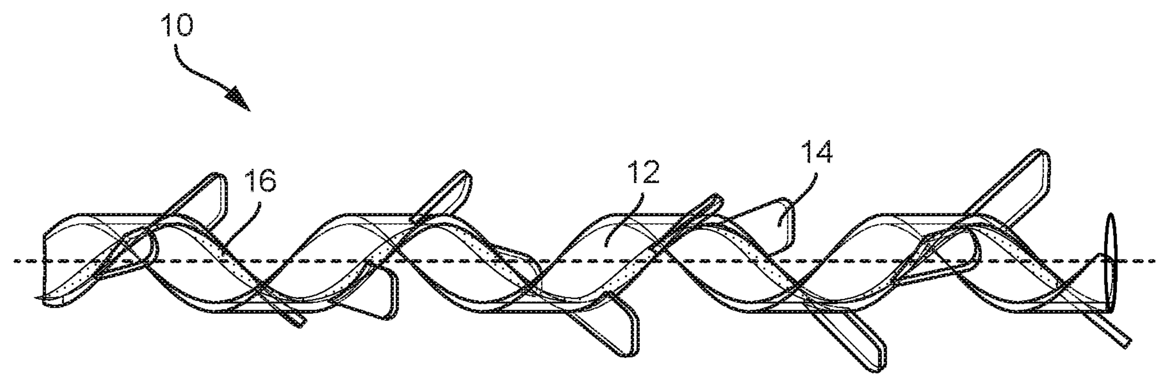
FIGS. 11A-11B illustrate an example anchor structure, in accordance with aspects of the invention.
Figure 11B:
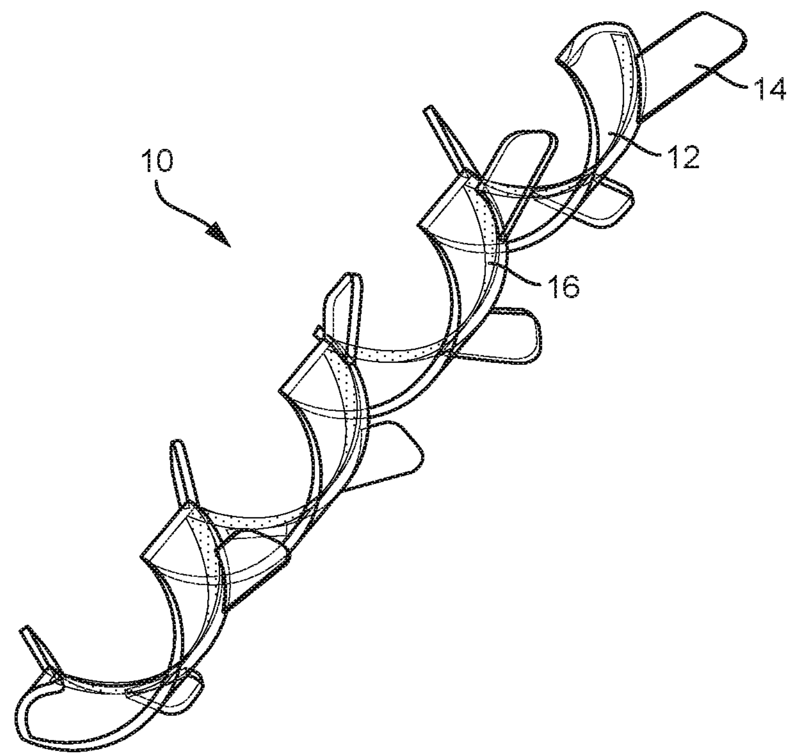

FIGS. 10A-10B and 11A-11B illustrate example anchors, similar to that shown in FIG. 8, except the tines 14 are formed in differing shapes. For example, in one aspect, the tines may be formed such that an end face is angled or pointed, such as shown in FIG. 8. In another aspect, the tines can be formed in a generally rectangular shape, such as shown in FIGS. 10A-10B. In another aspect, the tines can be formed such that the corners and/or edges are curved, rounded or chamfered, such as shown in FIGS. 11A-11B. This feature may help reduce the possibility of trauma to adjacent tissues by corners or edges of the tines as they engage tissue during anchoring of the lead.

Figure 12A:
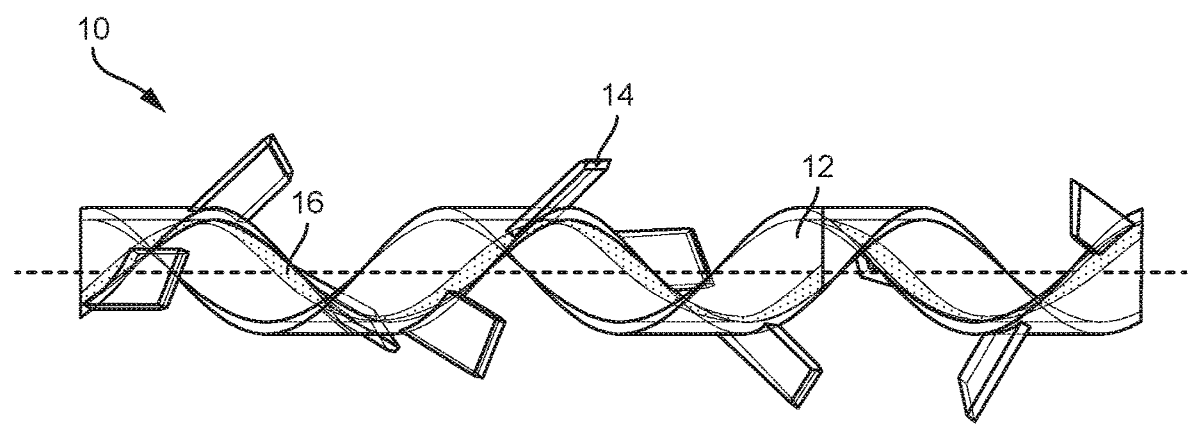
FIGS. 12A-12B illustrate an example anchor structure, in accordance with aspects of the invention.
Figure 12B:
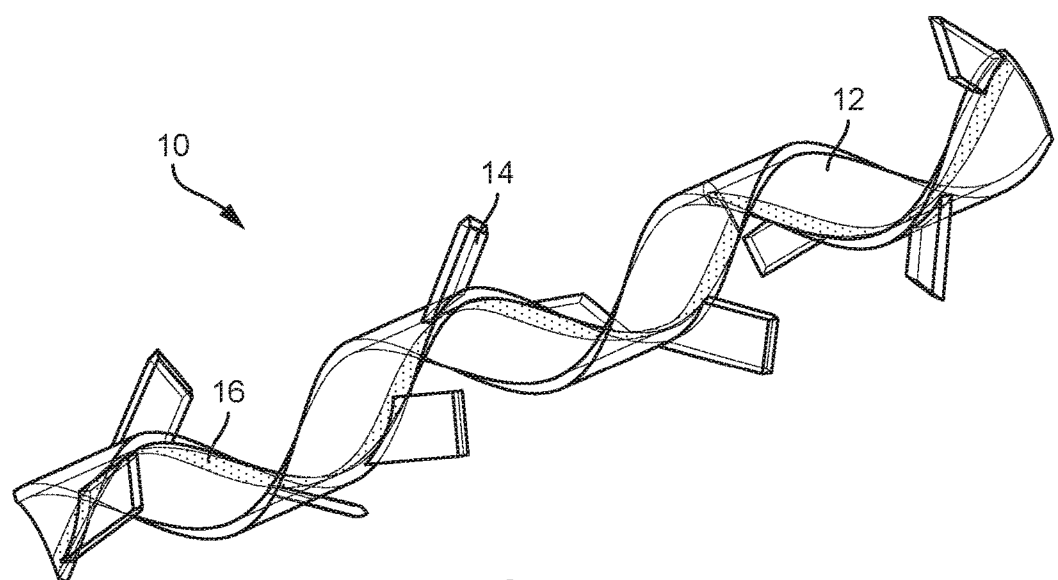

FIGS. 12A-12B illustrate an example anchor similar to that in FIG. 8 except the plurality of tines angle in both proximal and distal directions. As can be seen, the proximal most tines angle in a distal direction, while the remaining tines angle in a proximal direction. This aspect is useful in applications where the lead tends to experience forces in both proximal and distal directions. For example, while studies have shown that neurostimulation leads implanted through a sacral foramen experience primarily forces directed in a proximal direction, various other applications, such as a peripherally implanted lead in an arm or leg, may experience significant forces in both proximal and distal directions.

Figure 13A:
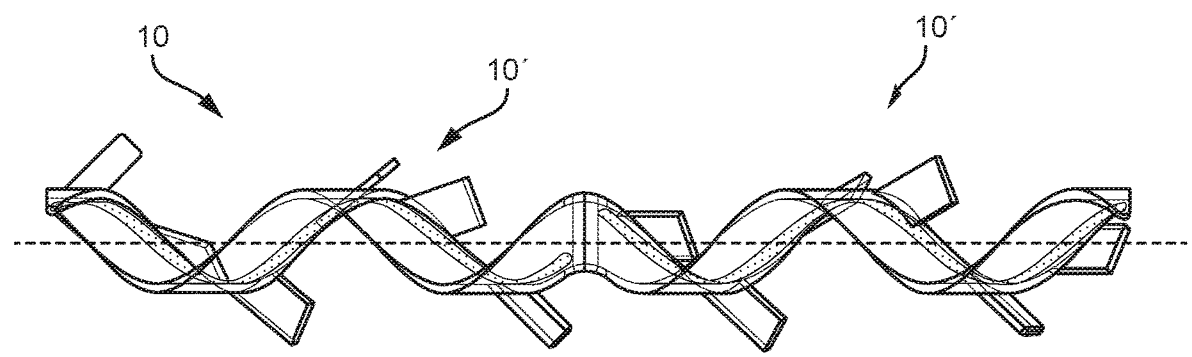
FIGS. 13A-13B illustrate an example anchor structure, in accordance with aspects of the invention.
Figure 13B:
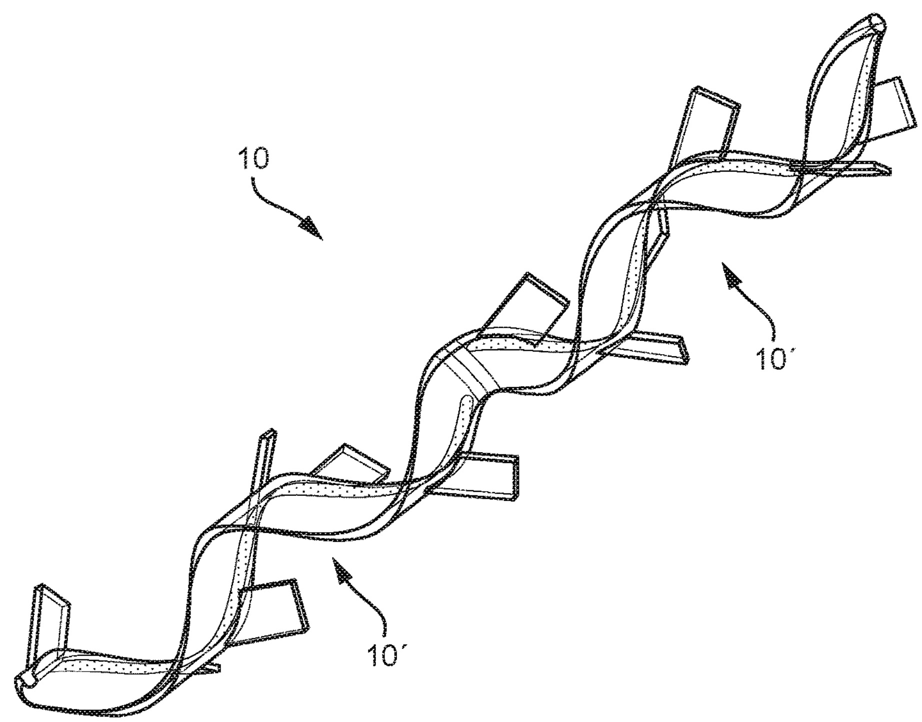

FIGS. 13A-13B illustrate an anchor 10 composed of multiple anchor sections 10'. As shown, the anchor consists of two sections joined together. The anchor sections 10' may be modular allowing one or more anchor sections to be used on a lead, as needed for a particular lead or application. The anchor sections may include a means to attach or couple the sections to one another or may be bonded together by various methods known to one of skill in the art, such as by use of an adhesive, a mechanical or chemical coupling, or an oxidation bonding method. This feature may allow a user to customize an anchoring portion with as desired, according to differing lengths, as well as differing dimensions and/or directions of the tines.

Figures 14A, 14B:
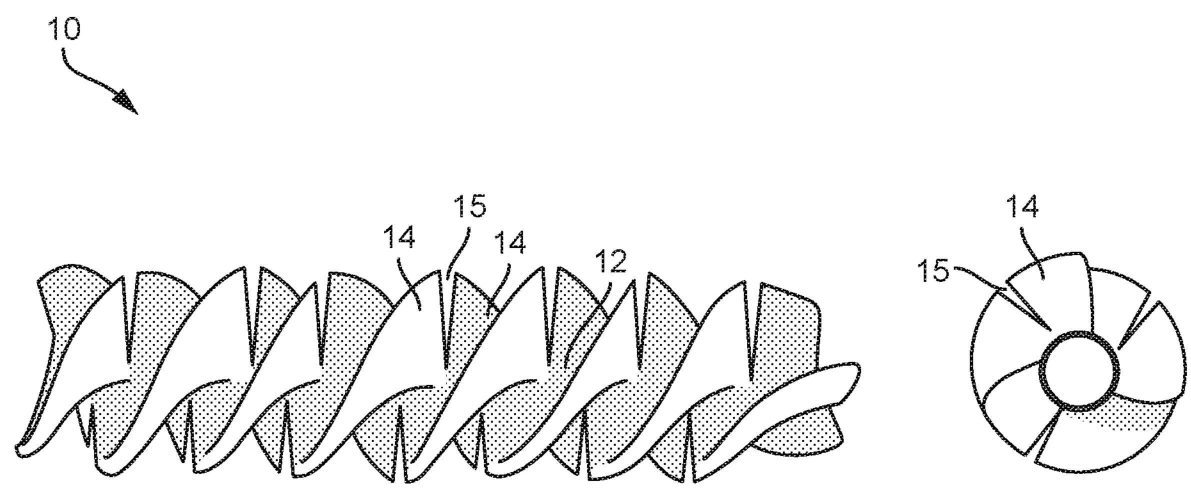
FIGS. 14A-14B illustrate an example anchor structure, in accordance with aspects of the invention.

FIG. 14A-14B illustrates an anchor 10 having a corkscrew type shape. The anchor includes a continuous helical flap having multiple sections defined by cuts into the helical flap into multiple sections that can fold toward the lead body without overlapping one another. In one aspect, the anchor 10 is formed from monolithically from a single integral component. For example, the anchor 10 may be formed from a cork-screw type structure in which the helical flap is separated into tines by wedge-shaped notches 15 cut into the helical flap to define multiple tines 14 that can fold down against the lead for delivery of the anchor through a constraining insertion sheath.

In another aspect, any of the anchors described herein may include one or more various other features, including: biodegradable tines, drug eluting tines, and flexible dish-like tines that open or collapse after a certain bend angle is reached to allow for easy insertion or retraction. In another aspect, the anchor may include a strip or embedded material that shield or disrupts MRI induced heating.

In one aspect, the anchor 10 includes one or more drug eluting components, that release one or more therapeutic compounds over a period of time after implantation. Such a drug eluting component may include a portion of the anchor, a strip intertwined along a length of the anchor, the material from which the anchor is formed, or a coating deposited on the anchor or portion thereof. For example, the drug or therapeutic compound can be sprayed onto the anchor, the anchor can be dipped in the drug or compound, or the drug or compound can be mixed into a polymer of which the anchor is formed. In some embodiments, the anchor may be formed of a bioabsorable or nonabsorable polymer material or a combination of a nonabsorable base coated with a layer of drug eluting polymer. In one aspect, the drug or therapeutic compound may be applied in order to promote release of the drug in particular direction, for example the drug or compound may be applied to promote isotropic or anisotropic release of the drug along the axis of the tines. The eluting drug may be selected to promote and shorten healing time in order to minimize risk of lead migration. Alternatively or in addition to, the anchor may be configured to elute various other drugs to provide various other therapeutic benefits. For example, the anchor 10 may be formed to elute a compound to promote fixation within the tissues, such as a biological adhesive or compound to promote tissue formation after implantation in order to further minimize risk of lead migration.

While in many of the embodiments shown, the tines are configured to protrude and fold along an axis parallel to the longitudinal axis along which the helical portion extends, in some embodiments, the anchor can be designed so that the tines fold inward along a helical or inclined axis. Such a configuration can allow the tines to be retracted by twisting the lead in one direction to facilitate removal of the lead and/or allow the tines to be further deployed by twisting the lead in an opposite direction. In other embodiments, such as those in which the tines fold along an axis parallel to the longitudinal axis, the tines may be sufficiently flexible and/or frangible to allow removal of the lead by merely retracting the lead with sufficient force.

Figure 15A:
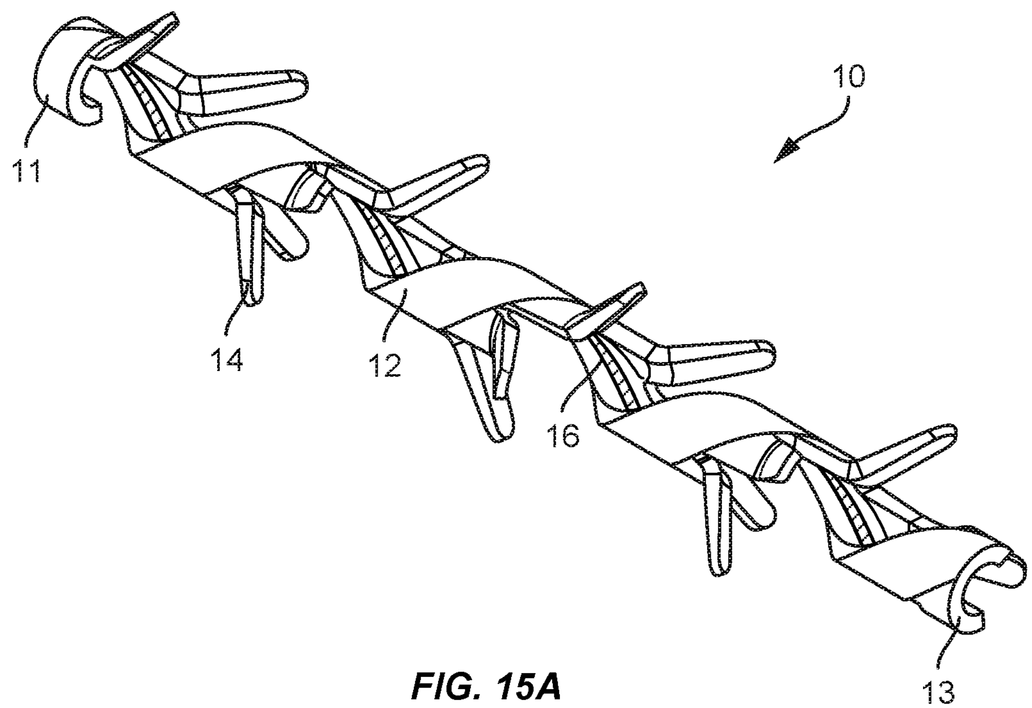
FIGS. 15A-15C illustrate an example anchor structure before and after deployment and FIG. 15C illustrates an end view of the deployed anchor structure, in accordance with aspects of the invention.
Figure 15B:
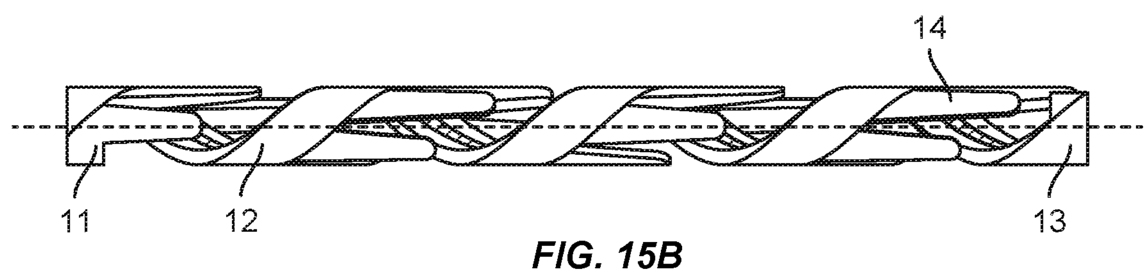
Figure 15C:
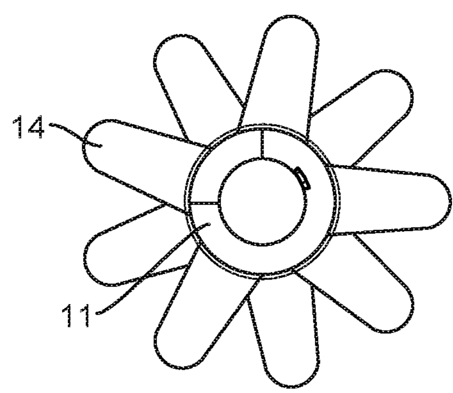

In one aspect, the anchor may be formed by cutting a pattern into an integral piece of material, for example a shape-memory metal, such as Nitinol. For example, the anchor can be formed by laser cutting a helical pattern into a piece of tubing or a cylindrical piece of the material, the pattern corresponding to the anchor in the constrained configuration, such as shown in the example of FIG. 15B. The tines can then be supported on a mold or propped up by various other means so that the material can be heat set while the anchor is in the expanded configuration, such as shown in FIG. 15A. Typically, the pattern is defined so that the tines are distributed evenly along the length of the helical body with the tines extending out in a multi-radial direction along the sweep of the spiral to provide evenly distributed tissue fixation in all directions, as shown in FIG. 15C.

In one aspect, the helical base can be heat set to a smaller inside diameter than the lead body so as to provide an interference fit, which can then be twisted to open and then loaded onto the lead body. Upon release, the helical base automatically tightens onto the lead body providing a secure attachment to the lead. The spiral design is configured so that when the tines are folded down the tines do not overlap each other or the helical body of the anchor.

In another aspect, as shown in FIG. 15A, the anchor design can include one or more retention features 11, 13 at the proximal and distal ends, respectively, that enable precise loading of the anchor onto the device. In this embodiment, the proximal and distal retention features 11,13 are designed to abut against a corresponding proximal and distal end of a reduced diameter anchoring portion 22 of the lead in which the anchor 10 is received so as to affix the anchor 10 to the body of the lead 20 and prevent axial movement of the anchor 10 along the lead before, during and/or after delivery of the lead and deployment of the anchor 10. In another aspect, the proximal and distal retention features 11, 13 may be designed in various shapes (e.g. zig-zag, curved, angled) along the proximal and distal facing edges so as to interlock with corresponding shapes along the lead at the proximal and distal ends of the anchoring portion 22. This configuration is useful in preventing free rotational movement of the anchor 10 relative the lead body 20 or to assist in translating rotational movement to the anchor upon rotation of the lead.

In one aspect, the anchor 10 may be formed of any type of implantable biocompatible polymers. Radiopaque fillers such as barium sulfate, bismuth, and tungsten can be added to the polymer to make the tines radiopaque under x-ray. Alternatively, or in addition to, a ribbon of radiopaque metal such as gold or platinum can be imbedded into the body of the helix to add radiopacity to the tines. In another approach, the anchor may include one or more discrete radiopaque markers that can be used with visualization techniques for localization of the anchor or that can be used to determine when the tines are deployed. For example, by placing one of a pair of markers at the end of a tine and the other on the helical body directly adjacent the end of the tine, when the anchor is in the constrained configuration, separation of the pair of markers can indicate when the tines are deployed, as well as the extent of their deployment within the tissue.

Figure 16A:
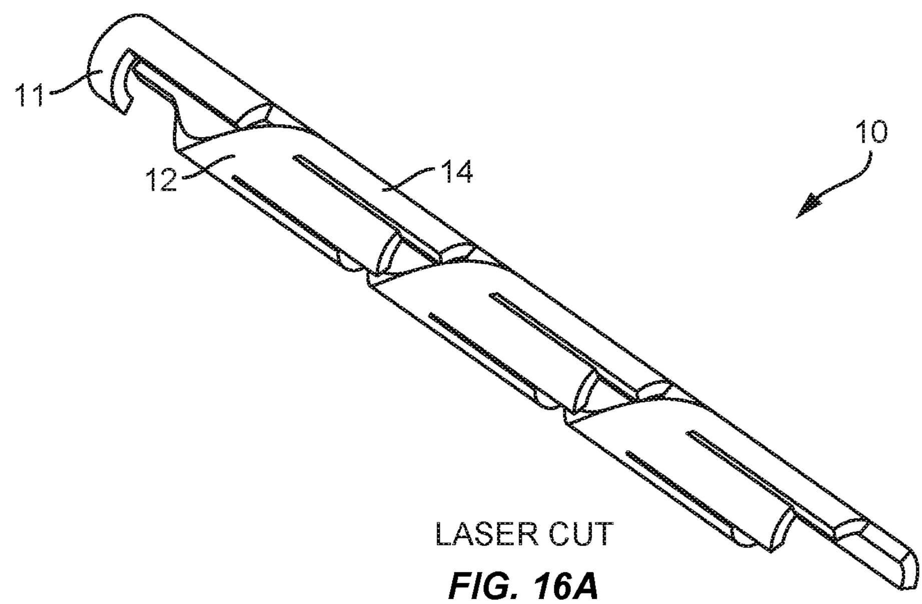
FIGS. 16A-16B illustrate an example anchor structure formed by laser cutting, the structure shown before and after deployment, in accordance with aspects of the invention.
Figure 16B:
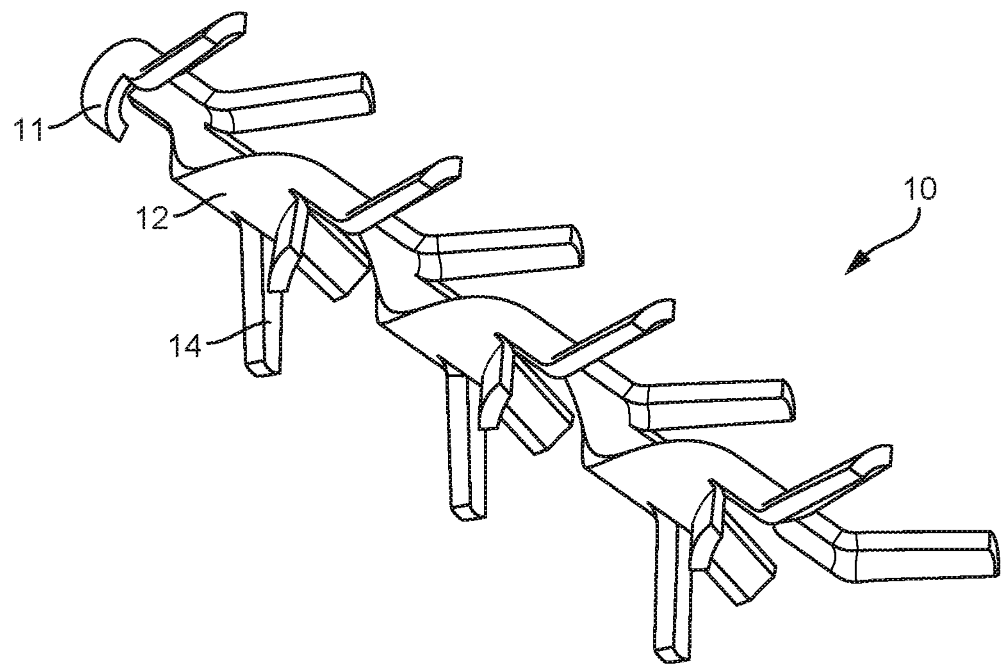

FIG. 16A illustrate another approach by which the anchor 10 can be formed. As shown in FIG. 16A, the anchor may be cut from a length of extruded polymer tubing, for example by laser cutting. The tines can be subsequently shaped to have an outwardly protruding bias through a heat set or reflow process. For example, the anchor 10 can be mounted on an internal mold (not shown) that props up the tines in an outwardly protruding configuration corresponding to the deployed anchor configuration and the polymer is heated and allowed to set. After setting, the tines 14 of the anchor 10 are biased towards the deployed configuration, such as shown in FIG. 16B. In one aspect, this heating and reflow process can also be used to incorporate one or more radiopaque markers, such as a Pt/Ir wire or ribbon wrapped at the same pitch as the helix. In another aspect, the polymer tubing extrusion can incorporate a ribbon or coil (e.g. nitinol or gold) ribbon to provide self expanding or self closure shape memory element to the anchor tines. Laser cutting can be programming to cut around the embedded ribbon wire to include the wire into the body of the helix.

Figure 17A:
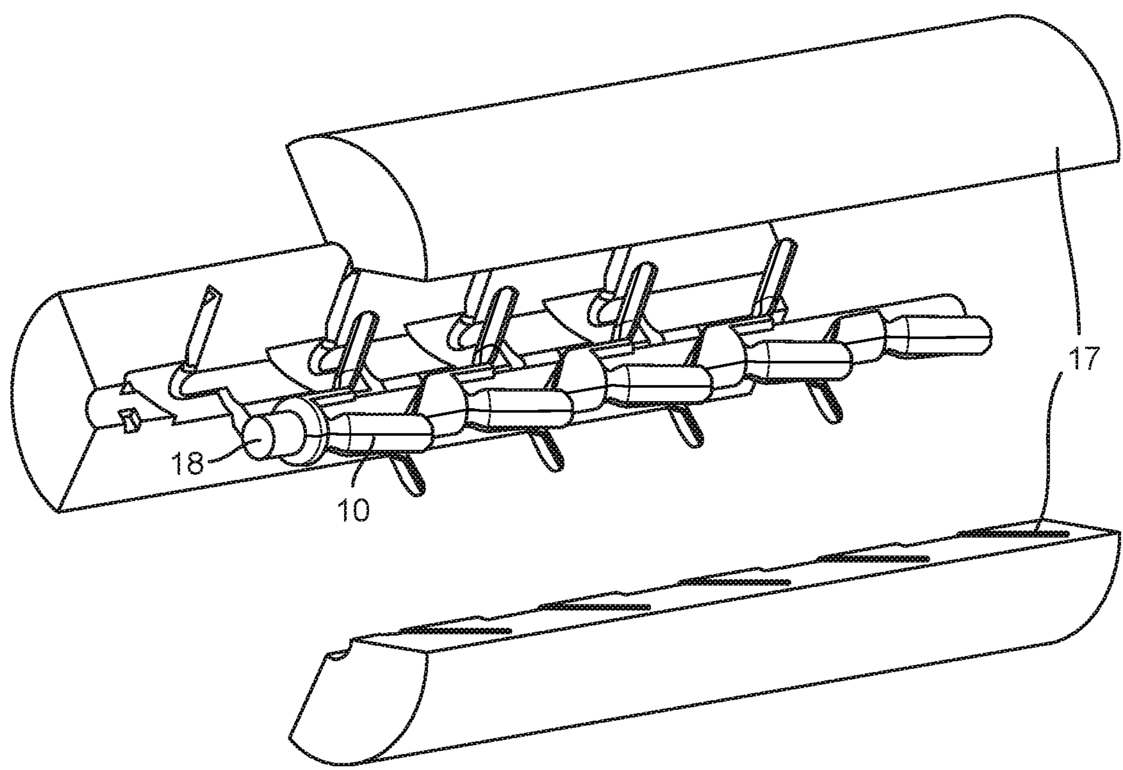
FIGS. 17A-17B illustrate an alternative illustrate an example anchor structure formed by an injection molding process, in accordance with aspects of the invention.
Figure 17B:
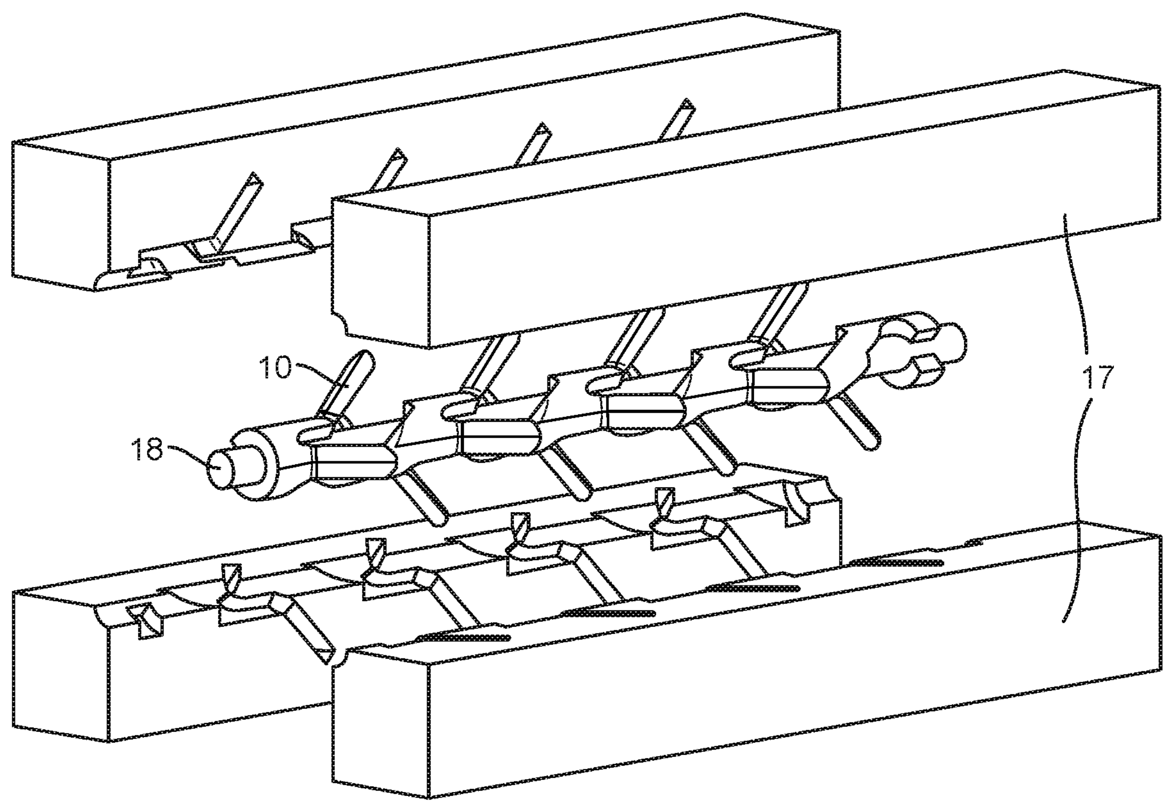

FIG. 17A-17B illustrate yet another approach by which the anchor 10 may be formed. Helical anchors, such as any of those described herein, can be formed by injection molding using a multi-piece mold design. For example, two, three or four piece mold designs can be used to mold the anchors as a single integral component. In one aspect, the mold can be configured so as to release the anchor at an angle that is specific to the design of the anchors. A shown in FIG. 17A, a three-piece mold 17 is used to form anchor 10 by an injection molding process. A core pin 18 is used along with the mold to form the open lumen of the anchor. FIG. 17B shows a four piece mold design 17' also configured for use with the core pin 18 to allow formation of an anchor 10 through an injection molding process. One advantage to using an injection molding process to form the anchor, is that molded anchors can have variable thickness along the length of the component. For example, such an anchor can be formed so that the base is thinner to improve crossing profile and the protruding tines are thicker to provide retention strength after implantation. In another aspect, a metallic element can be incorporated along the entire length, at the location of the tines, or in the distal and proximal ends for radiopacity.

Figure 18:
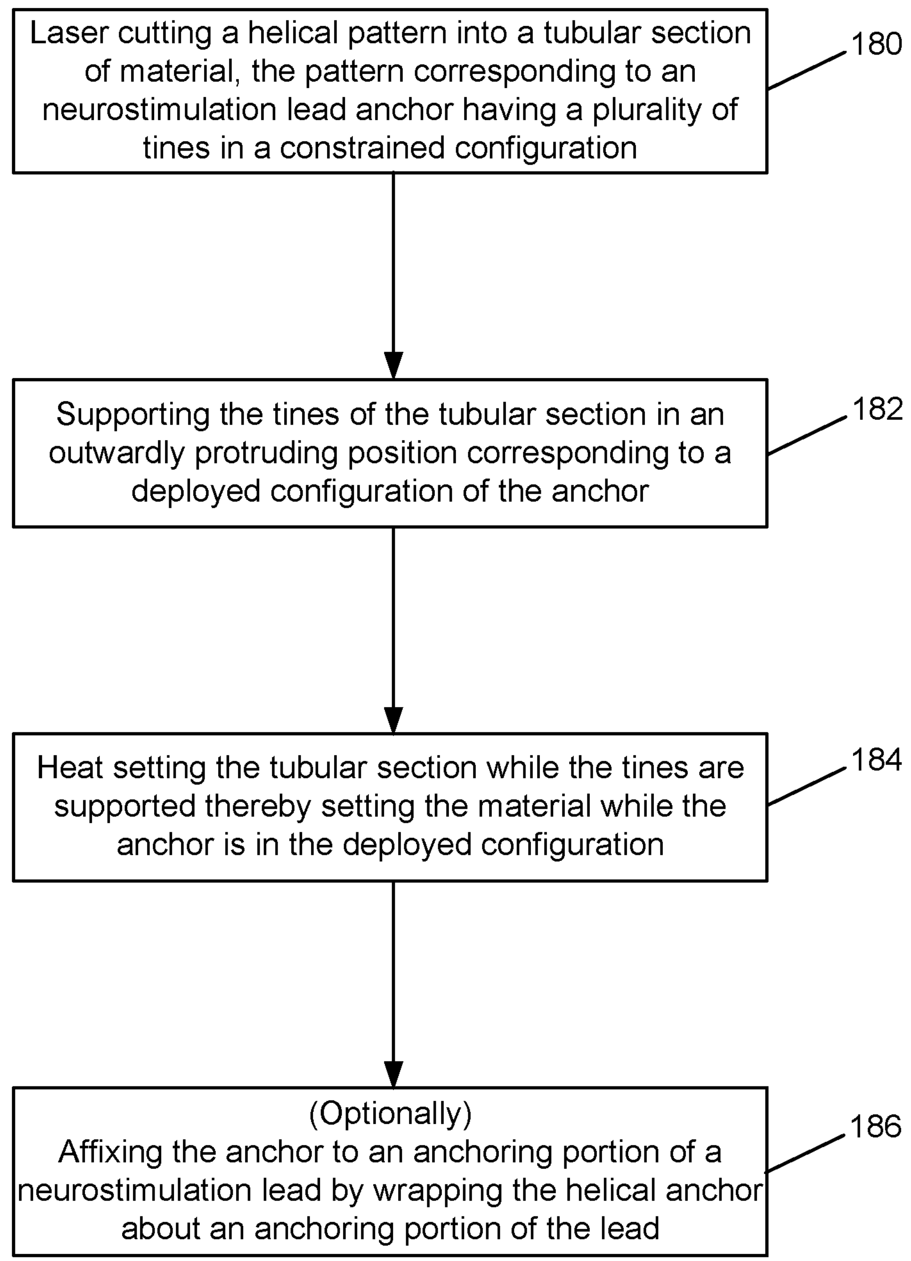
FIGS. 18-20 illustrate methods of forming an anchor and methods of anchoring a neurostimulation lead in accordance with aspects of the invention.
Figure 19:
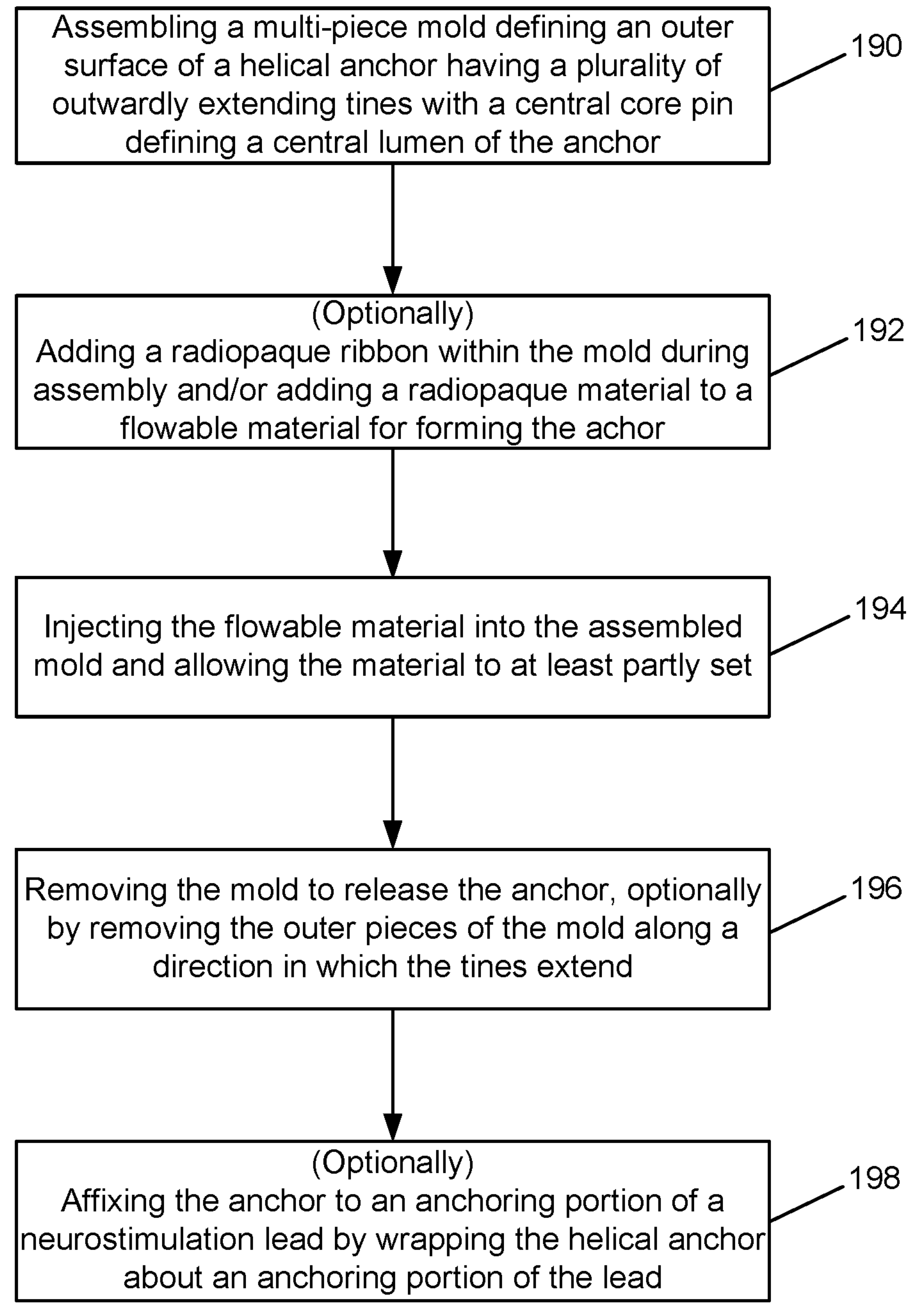

Methods of forming anchor in accordance with aspects of the invention described above are shown in the examples of FIG. 18-19. The example method of FIG. 18 includes method steps of: laser cutting a helical pattern into a tubular section of material, the pattern corresponding to an neurostimulation lead anchor having a plurality of tines in a constrained configuration 180; supporting the tines of the tubular section in an outwardly protruding position corresponding to a deployed configuration of the anchor 182; and heat setting the tubular section while the tines are supported thereby setting the material while the anchor is in the deployed configuration 184. In one aspect, the material is Nitinol, preferably in the superelastic phase and having an austenitic finish temperature from about 15 degrees C. to about 35 degrees C., so that the anchor will return to the deployed configuration upon heating in the body. In another aspect, the material may be formed of a polymer material that can be set in the deployed configuration by heating and reflow. The methods may be provided to a user to apply to the lead, or may be affixed to the lead before shipment to the user by wrapping the anchor about an anchoring portion 186. The example method of FIG. 19 includes steps of: assembling a multi-piece mold defining an outer surface of a helical anchor having a plurality of outwardly extending tines with a central core pin defining a central lumen of the anchor 190; injecting the flowable material into the assembled mold and allowing the material to at least partly set 194; and removing the mold to release the anchor 196. In some embodiments, the molds are configured such that the outer pieces of the mold are removed along a direction in which the tines extend, which reduces the stress and forces applied to the tines during removal. In some embodiments, a radiopaque ribbon within the mold during assembly and/or adding a radiopaque material to a flowable material for forming the anchor 192. Again, the anchor may be provided to the user for assembly with the lead or applied to the lead 198 and supplied to the user assembled with the lead. In another aspect, the anchor may be provided with the lead within a constraining sheath ready for insertion into the patient according to the implantation methods described herein.

Figure 20:
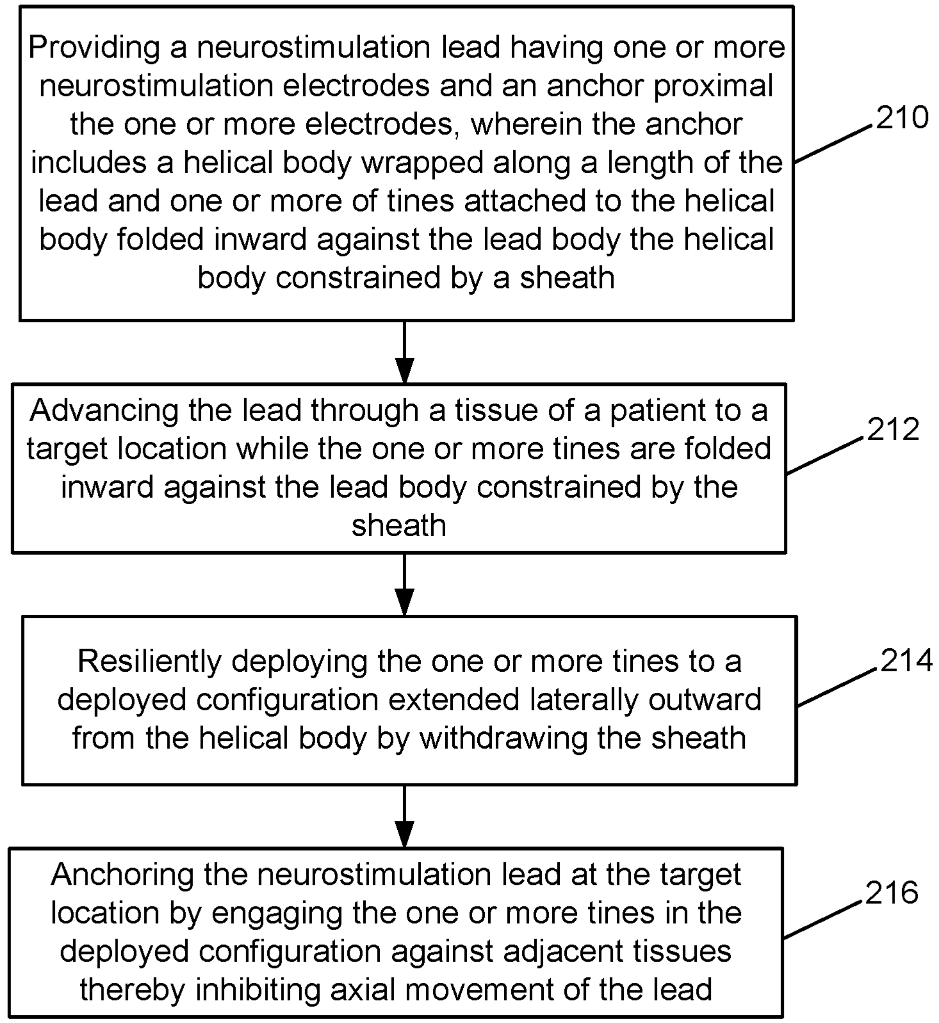

Methods of affixing an implanted neurostimulation lead using an anchor in accordance with aspects of the invention are show in the examples of FIGS. 20-21. The example method of FIG. 20 includes steps of: providing a neurostimulation lead having one or more neurostimulation electrodes and an anchor proximal the one or more electrodes, the anchor including a helical body wrapped along a length of the lead and one or more of tines attached to the helical body folded inward against the lead body the helical body constrained by a sheath 210; advancing the lead through a tissue of a patient to a target location while the one or more tines are folded inward against the lead body constrained by the sheath 212; resiliently deploying the one or more tines to a deployed configuration extended laterally outward from the helical body by withdrawing the sheath 214; and anchoring the neurostimulation lead at the target location by engaging the one or more tines in the deployed configuration against adjacent tissues thereby inhibiting axial movement of the lead 216. Lead removal may be effected by proximally withdrawing the lead until the anchoring force provided by the flexible tines is overcome. Thus, the tines are fabricated from a material having sufficient stiffness to provide a desired anchoring force but flexible enough to avoid tissue damage when withdrawn.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. An anchor for anchoring an implanted neurostimulation lead at a tissue location in a body of a patient, the anchor comprising:

a helical body extending helically along a longitudinal axis thereof; and a plurality of tines extending from the helical body, wherein each of the plurality of tines is biased toward a deployed configuration and resiliently deflectable for a delivery configuration, wherein the helical body and the plurality of tines are formed from a single integral tube, wherein in the deployed configuration, the plurality of tines extend laterally away from the longitudinal axis of the helical body, and in the delivery configuration, the plurality of tines are folded inward toward the longitudinal axis of the helical body to facilitate delivery of a lead during implantation, and wherein the anchor is molded from a polyurethane based material having a shore hardness in a range between 50A and 80D.

2. The anchor of claim 1, wherein the anchor is configured such that when attached to a lead body in the delivery configuration, each of the plurality of tines is configured to be folded directly against the lead body.

3. The anchor of claim 2, wherein each of the plurality of tines is configured to be folded against the lead body without overlapping a section of the helical body.

4. The anchor of claim 1, wherein the plurality of tines are substantially flush with the helical body of the anchor when in the delivery configuration.

5. The anchor of claim 1, wherein each of the plurality of tines has a rectangular shape.

6. The anchor of claim 1, wherein the anchor is dimensioned such that, when attached to a lead body and in the delivery configuration, the anchor has a cross sectional profile sufficiently small to facilitate delivery through a 5 French sheath.

7. The anchor of claim 1, wherein the helical body and the plurality of tines are integrally formed of a common material.

8. The anchor of claim 1, wherein the anchor is formed of a material with sufficient stiffness so that, when attached to an implanted lead and in the deployed configuration, engagement of tissue with the plurality of tines inhibits axial movement of the implanted lead when implanted in a tissue of the patient at a target location.

9. The anchor of claim 1, wherein, in the deployed configuration, each of the plurality of tines is angled in a proximal direction.

10. An anchor for anchoring an implanted neurostimulation lead at a tissue location in a body of a patient, the anchor comprising:

a helical body extending helically along a longitudinal axis thereof; and a plurality of tines extending from the helical body, wherein each of the plurality of tines is biased toward a deployed configuration and resiliently deflectable for a delivery configuration, wherein in the delivery configuration, the plurality of tines are substantially flush with the helical body, wherein in the deployed configuration, the plurality of tines extend laterally away from the longitudinal axis of the helical body, and in the delivery configuration, the plurality of tines are folded inward toward the longitudinal axis of the helical body to facilitate delivery of a lead during implantation, and wherein the anchor is molded from a polyurethane based material having a shore hardness in a range between 50A and 80D.

11. The anchor of claim 10, wherein the anchor is configured such that when attached to a lead body in the delivery configuration, each of the plurality of tines is configured to be folded directly against the lead body.

12. The anchor of claim 11, wherein each of the plurality of tines is configured to be folded against the lead body without overlapping a section of the helical body.

13. The anchor of claim 10, wherein each of the plurality of tines has a rectangular shape.

14. The anchor of claim 10, wherein the anchor is dimensioned such that, when attached to a lead body and in the delivery configuration, the anchor has a cross sectional profile sufficiently small to facilitate delivery through a 5 French sheath.

15. The anchor of claim 10, wherein the helical body and the plurality of tines are integrally formed of a common material.

16. The anchor of claim 10, wherein the anchor is formed of a material with sufficient stiffness so that, when attached to an implanted lead and in the deployed configuration, engagement of tissue with the plurality of tines inhibits axial movement of the implanted lead when implanted in a tissue of the patient at a target location.

17. The anchor of claim 10, wherein, in the deployed configuration, each of the plurality of tines is angled in a proximal direction.

18. The anchor of claim 10, wherein, in the deployed configuration, each of the plurality of tines extend laterally outward from the longitudinal axis at an angle between 30 and 80 degrees from the longitudinal axis.

* * * * *